(12) United States Patent
Cussenot et al.

(10) Patent No.: US 12,123,058 B2
(45) Date of Patent: Oct. 22, 2024

(54) MOLECULAR SIGNATURE AND USE THEREOF FOR THE IDENTIFICATION OF INDOLENT PROSTATE CANCER

(71) Applicants: SORBONNE UNIVERSITE, Paris (FR); CTRE RECHERCHE PATHOLOGIES PROSTATIQUES, Paris (FR); LIGUE NATIONALE CONTRE LE CANCER, Paris (FR); ASSISTANCE PUBLIQUE HOPITAUX DE PARIS, Paris (FR); INSERM (INSTITUT NATIONAL DE LA SANTÉ ET DE LA RECHERCHE MÉDICALE), Paris (FR); UNIVERSITÉ DE TOURS, Tours (FR); CENTRE HOSPITALIER RÉGIONAL UNIVERSITAIRE DE TOURS, Tours (FR)

(72) Inventors: Olivier Cussenot, Paris (FR); Aurélie Kamoun, Paris (FR); Aurélien De Reynies, Paris (FR); Géraldine Cancel-Tassin, Soisy-sur-Seine (FR); Gaëlle Fromont-Hankard, Luynes (FR)

(73) Assignees: SORBONNE UNIVERSITE, Paris (FR); CTRE RECHERCHE PATHOLOGIES PROSTATIQUES, Paris (FR); LIGUE NATIONALE CONTRE LE CANCER, Paris (FR); ASSISTANCE PUBLIQUE HOPITAUX DE PARIS, Paris (FR); INSERM (INSTITUT NATIONAL DE LA SANTÉ ET DE LA RECHERCHE MÉDICALE), Paris (FR); UNIVERSITÉ DE TOURS, Tours (FR); CENTRE HOSPITALIER RÉGIONAL UNIVERSITAIRE DE TOURS, Tours (FR)

( * ) Notice: Subject to any disclaimer, the term of this patent is extended or adjusted under 35 U.S.C. 154(b) by 1127 days.

(21) Appl. No.: 16/963,948

(22) PCT Filed: Jan. 25, 2019

(86) PCT No.: PCT/EP2019/051870
§ 371 (c)(1),
(2) Date: Jul. 22, 2020

(87) PCT Pub. No.: WO2019/145483
PCT Pub. Date: Aug. 1, 2019

(65) Prior Publication Data
US 2021/0040563 A1   Feb. 11, 2021

(30) Foreign Application Priority Data
Jan. 25, 2018  (EP) .................... 18305060

(51) Int. Cl.
C12Q 1/6886  (2018.01)
(52) U.S. Cl.
CPC ...... *C12Q 1/6886* (2013.01); *C12Q 2600/118* (2013.01); *C12Q 2600/154* (2013.01); *C12Q 2600/158* (2013.01)
(58) Field of Classification Search
None
See application file for complete search history.

(56) References Cited

U.S. PATENT DOCUMENTS

| | | |
|---|---|---|
| 2014/0303002 A1 | 10/2014 | Shak et al. |
| 2016/0097105 A1* | 4/2016 | Shak et al. ........... C12Q 1/6886 435/6.12 |

FOREIGN PATENT DOCUMENTS

WO     2011082198 A2     7/2011

OTHER PUBLICATIONS

Barbieri, C.E., et al. Exome sequencing identifies recurrent SPOP, FOXA1 and MED12 mutations in prostate cancer. Nature Genetics. May 20, 2012; 44(6):685-9.
The Cancer Genome Atlas Research Network. The Molecular Taxonomy of Primary Prostate Cancer. Cell. Nov. 5, 2015; 163(4):1011-25.
Catalona, W.J., et al. Comparison of digital rectal examination and serum prostate specific antigen in the early detection of prostate cancer: results of a multicenter clinical trial of 6,630 men. The Journal of Urology. May 1994; 151(5):1283-90.
Chaux, A., et al. Immunohistochemistry for ERG Expression as a Surrogate for TMPRSS2-ERG Fusion Detection in Prostatic Adenocarcinomas. Am J Surg Pathol. Jul. 2011; 35(7):1014-20.
Chen, YA, et al. Discovery of cross-reactive probes and polymorphic CpGs in the Illumina Infinium HumanMethylation450 microarray. Epigenetics. Feb. 2013; 8(2):203-9.
Cooperberg, M. R., et al. The University of California, San Francisco Cancer of the Prostate Risk Assessment Score: A Straightforward and Reliable Preoperative Predictor of Disease Recurrence after Radical Prostatectomy. The Journal of Urology. Jun. 2005; 173(6):1938-42.

(Continued)

*Primary Examiner* — Kaijiang Zhang
(74) *Attorney, Agent, or Firm* — Maier & Maier, PLLC

(57) ABSTRACT

A method for predicting the risk of prostate cancer recurrence in a subject affected with prostate cancer, including: (a) providing a sample from the subject, (b) determining the TMPRSS/ERG fusion status of the sample, (c) if the sample is positive for TMPRSS/ERG fusion (Fus⁺), determining a molecular signature of the sample by measuring the expression level of at least 6 prostate cancer markers selected from the ANPEP, AZGP1, CHRNA2, COMP, KHDRBS3 and SFRP4, (d) comparing the molecular signature to a reference signature, and (e) assigning the subject to a risk group based on the correlation of the molecular signature with the reference signature, thereby predicting the risk of cancer recurrence in the subject.

12 Claims, 9 Drawing Sheets
Specification includes a Sequence Listing.

(56) References Cited

OTHER PUBLICATIONS

Cuzick, J., et al. Prognostic value of a Combined Estrogen Receptor, Progesterone Receptor, Ki-67, and Human Epidermal Growth Factor Receptor 2 Immunohistochemical Score and Comparison With the Genomic Health Recurrence Score in Early Breast Cancer. Journal of Clinical Oncology. Nov. 10, 2011; 29(32):4273-8.
Dabney, A.R. Classification of microarrays to nearest centroids. Bioinformatics. Nov. 15, 2005; 21(22):4148-54.
D'Amico, A.V., et al. Biochemical Outcome After Radical Prostatectomy, External Beam Radiation Therapy, or Interstitial Radiation Therapy for Clinically Localized Prostate Cancer. JAMA. Sep. 16, 1998; 280(11):969-74.
Fraser, M., et al. Genomic hallmarks of localized, non-indolent prostate cancer. Nature. Jan. 19, 2017; 541(7637):359-364.
Gasi Tandefelt, D., et al. A 36-gene Signature Predicts Clinical Progression in a Subgroup of ERG-Positive Prostate Cancers. European Association of Urology. Dec. 2013; 64(6):941-50.
Gleason, D. F., et al. Prediction of prognosis for prostatic adenocarcinoma by combined histological grading and clinical staging. The Journal of Urology. Jan. 1974; 111(1):58-64.
Hanzelmann, S., et al. GSVA: gene set variation analysis for microarray and RNA-Seq data. BMC Bioinformatics. Jan. 16, 2013; 14:7.
Irshad, S., et al. A Molecular Signature Predictive of Indolent Prostate Cancer. Sci Transl Med. Sep. 11, 2013; 5(202):202ra122.
Jia, ZY., et al. Expression Changes in the Stroma of Prostate Cancer Predict Subsequent Relapse. PLoS One. 2012; 7(8):e41371.
Knezevic, D., et al. Analytical validation of the Oncotype DX prostate cancer assay—a clinical RT-PCR assay optimized for prostate needle biopsies. BMC Genomics. Oct. 8, 2013; 14:690.
Koo, K. M., et al. A simple, rapid, low-cost technique for naked-eye detection of urine-isolated TMPRSS2:ERG gene fusion RNA. Sci Rep. Jul. 29, 2016; 6:30722.
Kulkarni, M. M. Digital Multiplexed Gene Expression Analysis Using the NanoString nCounter System. Curr Protoc Mol Biol. Apr. 2011; Chapter 25:Unit25B.10.
Maher, C. A., et al. Transcriptome sequencing to detect gene fusions in cancer. Nature. Mar. 5, 2009; 458(7234):97-101.
Malkov, V. A., et al. Multiplexed measurements of gene signatures in different analytes using the Nanostring nCounter Assay System. BMC Res Notes. May 9, 2009; 2:80.
Mertz, K. D., et al. Molecular Characterization of TMPRSS2-ERG Gene Fusion in the NCI-H660 Prostate Cancer Cell Line: A New Perspective for an Old Model. Neoplasia. Mar. 2007; 9(3):200-6.
Narod S.A., et al. Fusion in the ETS gene family and prostate cancer. British Journal of Cancer. Sep. 16, 2008; 99(6):847-51.
Popova, T., et al. Genome Alteration Print (GAP): a tool to visualize and mine complex cancer genomic profiles obtained by SNP arrays. Genome Biology. 2009; 10(11):R128.
Ritchie, M. E., et al. limma powers differential expression analyses for RNA-sequencing and microarray studies. Nucleic Acids Research. Apr. 20, 2015; 43(7):e47.
Ross-Adams, H., et al. Integration of copy number and transcriptomics provides risk stratification in prostate cancer: A discovery and validation cohort study. EBioMedicine. Jul. 29, 2015; 2(9):1133-44.
Setlur, S. R., et al. Estrogen-Dependent Signaling in a Molecularly Distinct Subclass of Aggressive Prostate Cancer. J Natl Cancer Inst. Jun. 4, 2008; 100(11):815-25.
Shen, Q., et al. New gene selection method for multiclass tumor classification by class centroid. Journal of Biomedical Informatics. Feb. 2009; 42(1):59-65.
Staaf, J., et al. Normalization of Illumina Infinium whole-genome SNP data improves copy number estimates and allelic intensity ratios. BMC Bioinformatics. Oct. 2, 2008; 9:409.
Taylor, B. S., et al. Integrative Genomic Profiling of Human Prostate Cancer. Cancer Cell. Jul. 13, 2010; 18(1):11-22.
Tibshirani, R., et al. Diagnosis of multiple cancer types by shrunken centroids of gene expression. Proc Natl Acad Sci U S A. May 14, 2002; 99(10):6567-72.
Tomlins, S. A., et al. Recurrent Fusion of TMPRSS2 and ETS Transcription Factor Genes in Prostate Cancer. Science. Oct. 28, 2005; 310(5748):644-8.
Venkatraman, E. S. and Olshen, A.B. A faster circular binary segmentation algorithm for the analysis of array CGH data. Bioinformatics. Mar. 15, 2007; 23(6):657-63.
Wilkerson, M. D. and Hayes, D. N. ConsensusClusterPlus: a class discovery tool with confidence assessments and item tracking. Bioinformatics. Jun. 15, 2010; 26(12):1572-3.
Zhang, NQ, et al. Predicting tumor purity from methylation microarray data. Bioinformatics. Nov. 1, 2015; 31(21):3401-5.
"HuGene-1_0-st] Affymetrix Human Gene 1.0 ST Array [transcript (gene) version", GEO2007, retrieved from NCBI Database accession No. GPL6244.
"Illumina HumanHT-12 V4.0 expression beadchip", GEO17 Jun. 2010 (Jun. 17, 2010), retrieved from NCBI Database accession No. GPL 10558.

* cited by examiner

MOLECULAR SIGNATURE AND USE THEREOF FOR THE IDENTIFICATION OF INDOLENT PROSTATE CANCER

FIELD

The present invention relates to the field of cancer prognosis. More specifically, the present invention relates to a signature based on differential gene expression, for the prognosis of prostatic adenocarcinomas in a subject.

BACKGROUND

Prostate cancer (PCa) is a cancer of the prostate, characterized by unregulated and uncontrolled cell growth and division. PCa is one of the most frequent cancer diagnosed in men in developed countries, accounting for around 8% of all new cancer cases and 15% in men.

The clinical behavior of prostate cancer is highly variable: some men will have aggressive cancers leading to metastasis and death from the disease, while many others will have indolent cancers that are cured with initial therapy or may be safely observed. Multiple risk stratification systems have been developed, combining clinical and pathological parameters, such as D'Amico's classification (D'Amico et al., 1998. *JAMA.* 280(11):969-74) and CAPRA score, (Cooperberg et al., 2005. *J Urol.* 173(6):1938-42), blood Prostate Specific Antigen (PSA) levels (Catalona et al., 1994. *J Urol.* 151(5):1283-90), histological criteria such as Gleason score (Gleason & Mellinger, 1974. *J Urol.* 111(1):58-64) and TNM classification (based on tumor size, regional lymph nodes description and presence of metastasis).

However, in spite of these clinical classification systems, randomized studies on the management of localized PCa (Scandinavian Prostate Cancer Group Study Number 4 [SPCG-4], Prostate Cancer Intervention versus Observation Trial [PIVOT] and Prostate Testing for Cancer and Treatment [PROTECT]) have shown that 20% of PCa will progress to metastatic state and death after more than ten years of follow-up, suggesting that the majority of PCa which are diagnosed at the localized stage are exposed to overtreatment.

There remains thus a need for improved prognostic and predictive means to estimate for each subject the progression of the disease and the response to a given treatment.

The democratization of molecular and genomic profiling has considerably helped characterizing PCa molecular heterogeneity and find relevant markers. Various PCa subtype classifications have been proposed in the art, including the classification published by The Cancer Genome Atlas (TCGA) (Cancer Genome Atlas Research Network, 2015. *Cell.* 163(4):1011-25). This molecular taxonomy allows to classify 74% of PCa into one of seven subtypes defined by specific gene fusions or mutations, leaving a significant (26%) subset of prostate cancers of both good and poor clinical prognosis, unclassified. Currently, commercially available molecular tests designed to classify PCa and make treatment decisions include the OncotypeDX® Genomic Prostate Score assay by Genomics Health, Inc. (which provides a score based on clinical risk factors and expression of 17 genes), the Prolaris Test by Myriad Genetics, Inc. (which provides a score based on signature of cell cycle proliferation genes), the Proveri test by Proveri, Inc. (based on the expression level of 15 genes). Other approaches proposed by the scientific community include the prognosis signature developed by Isrhad et al. (2013. *Sci Transl Med.* 5(202):202ra122) (based on the expression of 19 genes) and the one by Tandefelt et al. (2013. *Eur Urol.* 64(6):941-50) (based on the expression of 36 genes).

However, the lack of consensus among published molecular classifications and prognostic molecular signatures makes it difficult to use the molecular characteristics within clinical routine. Moreover, current molecular signatures still leave some room for improvement of prognosis accuracy.

In spite of these recent advances, there is therefore still a need for an improved molecular signature that may be used for the identification of indolent cancer in PCa patients.

Here, the Inventors have surprisingly demonstrated that a classification integrating mRNA expression, DNA methylation and copy number data allows to define three subtypes of PCa, among which one subtype is strongly correlated to TMPRSS2/ERG fusion positive indolent PCa patients who could reasonably be handled with active surveillance rather than ongoing a radical life-changing surgery. Based on this new classification, the Inventors provide herein a molecular signature of 39 genes, and have further identified three minimal molecular signatures of 18, 15, 8 and 6 genes based thereon, constituting robust routine molecular assays to identify PCa which are not likely to evolve to a higher stage of the disease.

SUMMARY

The present invention relates to a method for predicting the risk of prostate cancer recurrence in a subject affected with prostate cancer, comprising:
a) providing a sample from said subject,
b) determining the TMPRSS/ERG fusion status in said sample,
c) if said sample is positive for TMPRSS/ERG fusion (Fus$^+$), determining a molecular signature of said sample by measuring the expression level of at least 6 prostate cancer markers selected from the group comprising ANPEP, AZGP1, CHRNA2, COMP, KHDRBS3 and SFRP4,
d) comparing said molecular signature to a reference signature, and
e) assigning the subject to a risk group based on the correlation of the molecular signature with the reference signature,
thereby predicting the risk of prostate cancer recurrence in said subject.

In one embodiment, the step of determining a molecular signature of said sample (step c) comprises measuring the expression level of at least 7, preferably at least 8 prostate cancer markers selected from the group comprising ANPEP, ANTXR1, AZGP1, CHRNA2, COMP, KHDRBS3, MS4A6A and SFRP4.

In one embodiment, the step of determining a molecular signature of said sample (step c) comprises measuring the expression level of the 8 following prostate cancer markers: ANPEP, ANTXR1, AZGP1, CHRNA2, COMP, KHDRBS3, MS4A6A and SFRP4.

In one embodiment, the step of determining a molecular signature of said sample (step c) comprises measuring the expression level of at least 8, preferably at least 15 prostate cancer markers selected from the group comprising ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In one embodiment, the step of determining a molecular signature of said sample (step c) comprises measuring the expression level of the 15 following prostate cancer markers: ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In one embodiment, the step of determining a molecular signature of said sample (step c) comprises measuring the expression level of at least 10, preferably at least 18 prostate cancer markers selected from the group comprising ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In one embodiment, the step of determining a molecular signature of said sample (step c) comprises measuring the expression level of the 18 following prostate cancer markers: ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In one embodiment, the step of determining a molecular signature of said sample (step c) comprises measuring the expression level of at least 39 prostate cancer markers selected from the group comprising ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In one embodiment, the step of determining a molecular signature of said sample (step c) comprises measuring the expression level of the 39 following prostate cancer markers: ACADL, AFF3, ANO7, ANPEP, ANTXR1, ASPN, AZGP1, CD38, CDH1, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In one embodiment, said sample is a prostate biopsy sample, a prostate fine-needle aspirate sample, a prostate resection sample or a prostate tissue sample after prostatectomy.

In one embodiment, said sample is a bodily fluid. In one embodiment, said bodily fluid is selected from the group comprising blood, plasma, serum, lymph, ascetic fluid, cystic fluid, urine, bile, nipple exudate, synovial fluid, bronchoalveolar lavage fluid, sputum, amniotic fluid, peritoneal fluid, cerebrospinal fluid, pleural fluid, pericardial fluid, semen, saliva, sweat and alveolar macrophages.

In one embodiment, the subject underwent prostatectomy and/or treatment by irradiation.

In one embodiment, the reference signature is derived from the measurement of the expression levels of prostate cancer markers in a reference population comprising at least 100, preferably at least 250, more preferably at least 500 subjects diagnosed with prostate cancer of known prostate cancer recurrence status.

In one embodiment, the subject is assigned to a low-risk of prostate cancer recurrence group, if the expression profile of ANPEP, AZGP1 and CHRNA2 is overexpressed with respect to a reference signature of a population of subjects diagnosed with aggressive prostate cancer, and the expression profile of COMP, KHDRBS3 and SFRP4 is underexpressed with respect to a reference signature of a population of subjects diagnosed with aggressive prostate cancer.

In one embodiment, the subject is assigned to a low-risk of prostate cancer recurrence group, if the expression profile of ANPEP, AZGP1 and CHRNA2 is overexpressed with respect to a reference signature of a population of subjects diagnosed with aggressive prostate cancer, and the expression profile of ANTXR1, COMP, KHDRBS3, MS4A6A and SFRP4 is under expressed with respect to a reference signature of a population of subjects diagnosed with aggressive prostate cancer.

In one embodiment, the subject is assigned to a low-risk of prostate cancer recurrence group, if the expression profile of ACADL, ANPEP, AZGP1, CHRNA2, FMOD, GPT2, NCAPD3, REPS2, SLC15A2 and SLC22A3 is overexpressed with respect to a reference signature of a population of subjects diagnosed with aggressive prostate cancer, and the expression profile of COL1A1, COMP, KHDRBS3, SFRP4 and VCAN is underexpressed with respect to a reference signature of a population of subjects diagnosed with aggressive prostate cancer.

In one embodiment, the subject is assigned to a low-risk of prostate cancer recurrence group, if the expression profile of ACADL, ANPEP, AZGP1, CHRNA2, FMOD, GPT2, NCAPD3, REPS2, SLC15A2 and SLC22A3 is overexpressed with respect to a reference signature of a population of subjects diagnosed with aggressive prostate cancer, and the expression profile of ANTXR1, COL1A1, COL3A1, COMP, ITGBL1, KHDRBS3, SFRP4 and SPARC is under expressed with respect to a reference signature of a population of subjects diagnosed with aggressive prostate cancer.

In one embodiment, the subject is assigned to a low-risk of prostate cancer recurrence group, if the expression profile of ACADL, AFF3, ANO7, ANPEP, AZGP1, CD38, CHRNA2, FAM3B, FMOD, GPT2, HGD, NCAPD3, REPS2, SLC15A2, SLC22A3 and STXBP6 is overexpressed with respect to a reference signature of a population of subjects diagnosed with aggressive prostate cancer, and the expression profile of ANTXR1, ASPN, CDH11, COL1A1, COL1A2, COL3A1, COL8A1, COL10A1, COMP, CPXM2, CXCL14, FRZB, ITGBL1, KHDRBS3, MGP, MS4A6A, NOX4, SFRP2, SFRP4, SPARC, SULF1, THBS2 and VCAN is underexpressed with respect to a reference signature of a population of subjects diagnosed with aggressive prostate cancer.

In one embodiment, the subject is assigned to a low recurrence risk group if the molecular signature of the sample from said subject has the highest correlation with respect to a reference signature of a population of subjects previously diagnosed with indolent prostate cancer.

The present invention further relates to a method for treating a subject affected with indolent prostate cancer, comprising the steps of:
a) predicting the risk of prostate cancer recurrence in a subject affected with prostate cancer according to the method for predicting the risk of prostate cancer recurrence in a subject affected with prostate cancer according to the present invention, and
b) placing said subject under active surveillance if the subject was assigned to a low risk group.

The present invention further relates to a kit for implementing the method for predicting the risk of prostate cancer recurrence in a subject affected with prostate cancer according to the present invention, wherein said kit consists of means for determining the expression levels of six prostate cancer markers selected from the group comprising ANPEP, AZGP1, CHRNA2, COMP, KHDRBS3 and SFRP4.

In one embodiment, the kit consists of means for determining the expression levels of 7, preferably 8 prostate cancer markers selected from the group comprising ANPEP, ANTXR1, AZGP1, CHRNA2, COMP, KHDRBS3, MS4A6A and SFRP4.

In one embodiment, the kit consists of means for determining the expression levels of 8, preferably 15 prostate cancer markers selected from the group comprising ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In one embodiment, the kit consists of means for determining the expression levels of 10, preferably 18 prostate cancer markers selected from the group comprising ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In one embodiment, the kit consists of means for determining the expression levels of 39 prostate cancer markers selected from the group comprising ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In one embodiment, said means for determining the expression levels is a microarray consisting of probes specific for said prostate cancer markers. In one embodiment, said probes specific for said prostate cancer markers are selected from the group comprising probes listed in Table 1 and/or Table 2.

In one embodiment, said means for determining the expression levels consist of qPCR primers specific for said prostate cancer markers.

DEFINITIONS

In the present invention, the following terms have the following meanings:

"Active surveillance" and "watchful waiting", as used herein, mean closely monitoring a subject's condition without giving any treatment until symptoms appear or change. For example, in prostate cancer, watchful waiting is usually used in older men with other medical problems, in early-stage disease or in diagnosed indolent prostate cancer cases.

"Biochemical recurrence (BCR)", as used herein, refers to a rise in the blood level of prostate-specific antigen (PSA) in PCa patients after treatment with surgery or radiation, indicating the presence of prostate cancer cells in a sample. Accordingly, the term "biochemical recurrence-free interval (bRFI)" is used to mean the time (in months or years) from surgery to first biochemical recurrence of prostate cancer. Clinical recurrences, losses due to incomplete follow-up, other primary cancers, or death prior to biochemical recurrence are considered censoring events.

"Clinical recurrence", as used herein, refers to the clinically-assessed (e.g., by imaging study or biopsy) presence of prostate cancer cells in a sample of a PCa patient after treatment with surgery or radiation. Accordingly, the term "clinical recurrence-free interval (cRFI)" is used herein as time (in months or years) from surgery to first clinical recurrence or death due to clinical recurrence of prostate cancer. Losses due to incomplete follow-up, other primary cancers or death prior to clinical recurrence are considered censoring events; when these occur, the only information known is that up through the censoring time, clinical recurrence has not occurred in this subject. Biochemical recurrences are ignored for the purposes of calculating cRFI.

"Expression", as used herein, refers to the expression of a marker, whether gene marker, RNA marker or protein marker. Expression of a marker may be determined at the protein level by ways of, e.g., immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA) and the like. Alternatively, expression of a marker may be determined at the mRNA level, by ways of, e.g., RT-PCR, RT-qPCR (wherein qPCR stands for quantitative PCR), hybridization techniques such as, for example, Northern Blot, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

"Marker", as used herein, broadly refers to all gene-linked substances that correlate with the expression level of a certain gene and/or allele. By way of example, included are a gene itself, its mRNA (a transcript of said gene), a peptide (its translated product), and a protein (the final product of expression of said gene). In one embodiment, each marker is identifiable as all or a portion of a gene and is therefore referred to as "gene marker". In one embodiment, each marker is identifiable as all or a portion of an mRNA and is therefore referred to as "RNA marker". In one embodiment, each marker is identifiable as all or a portion of a peptide or protein and is therefore referred to as "protein marker".

"Metastasis", as used herein, refers to a process in which cancer cells travel from one organ or tissue to another non-adjacent organ or tissue. Cancer cells in the prostate can spread to tissues and organs of a subject, and conversely, cancer cells from other organs or tissue can invade or metastasize to the prostate. Cancerous cells from the prostate may invade or metastasize to any other organ or tissue of the body. Prostate cancer cells often invade spine cells (e.g., vertebral column) and/or metastasize to the lungs, liver, and/or brain and spread cancer in these tissues and organs.

"Microarrays", "array" or "chip", as used herein, are interchangeable and refer to a 2-dimension (2D) array on a substrate, preferably a solid substrate, on which a plurality of probe molecules of specific nucleic acid and/or protein binding sequences has been affixed at separate locations in an ordered manner thus forming a microscopic array. Specific nucleic acid and/or protein binding sequences may be bound to the substrate of the chip through one or more different type of linker molecules. In a preferred embodiment, a microarray as used herein comprises specific nucleic acid binding sequences. In one embodiment, a microarray is used to assay large amounts of biological materials using high-throughput screening. Examples of microarrays include, but are not limited to, DNA microarrays, MMChips (for surveillance of microRNA populations), protein microarrays, peptide microarrays (for detailed analyzes or optimization of protein-protein interactions), tissue microarrays, transfection microarrays, chemical compound microarrays, antibody microarrays, glycan arrays, phenotype microarrays, reverse phase protein microarrays, microarrays of lysates or serum and interferometric reflectance imaging sensor (IRIS). "DNA microarrays", also commonly known as "DNA chips" or "biochips", include, without limitation, cDNA microarrays, oligonucleotide microarrays, BAC microarrays and SNP microarrays. In one embodiment, DNA microarrays are used to measure the expression levels of large numbers of genes simultaneously or to genotype multiple regions of a genome. In one embodiment, DNA microarrays are used to assess gene expression levels, comparative genomic hybridization, single nucleotide polymorphism (SNP) detection, alternative splicing detection, fusion genes, genome tilling and the like.

"Prognosis" refers to the likelihood of cancer-attributable death or cancer progression, including recurrence and metastatic spread of a neoplastic disease, during the natural history of the disease, or to the likelihood of a beneficial outcome whether following a specific treatment or not, wherein a beneficial response means an improvement in any measure of patient status including, but not limited to, overall survival, long-term survival (i.e., survival for at least 3, preferably at least 5, 8, or 10 years following diagnosis, surgery or other treatment), recurrence-free survival, and distant recurrence-free survival. Accordingly, a "good prognosis" or "positive prognosis" as used herein, refers to a beneficial clinical outcome such as long-term survival without recurrence; and a "bad prognosis" or "negative prognosis" refers to a negative clinical outcome such as cancer recurrence.

"Prostate cancer", as used herein, refers to a cancer in the prostate, a tubuloalveolar exocrine gland of the male reproductive system. Factors that increase the risk of developing a prostate cancer include, but are not limited to, older age, family history of prostate cancer and race. The World Health Organization estimates that about 99% of prostate cancer cases occur in men over the age of 50. Prostate cancers can be classified into two groups, depending on the affected cell type. Prostate adenocarcinoma is the first and main group of prostate cancer. It accounts for around 95% of prostate cancers, and develop from the acini of the prostatic ducts. They arise in the posterior/peripheral prostate gland more commonly (70%) than the anterior and central prostate gland (30%). The second group of prostate cancer, significantly less widespread with around 5% of the cases, is prostate sarcoma. This uncommon and heterogenous group of prostate cancers arises from mesenchymal cells in and around the prostate. Prostate sarcomas include, but are not limited to, rhabdomyosarcoma of the prostate, leiomyosarcoma of the prostate, sarcomatoid carcinoma of the prostate, malignant fibrous histiocytoma of the prostate, phyllodes tumor (also termed cystosarcoma phyllodes of the prostate) and undifferentiated stromal sarcoma of the prostate. Prostate cancer can have different clinical behaviors. As used herein, the term "indolent prostate cancer" is used to define a prostate cancer that is not likely to evolve to a higher stage of the disease. Such prostate cancers are also termed herein "low recurrence risk prostate cancer", "biochemical recurrence-free prostate cancers" or "non-relapsing prostate cancers". As used herein, the term "aggressive prostate cancer" is used to define a prostate cancer that is likely to evolve to a higher stage of the disease. Such prostate cancers are also termed "high recurrence risk prostate cancer", "biochemically recurrent prostate cancers" or "relapsing prostate cancers".

"Prostate cancer sample", as used herein, refers to a prostate tissue sample containing one or more cancer cells, or a fraction of one or more cancer cells. Those skilled in the art will recognize that such sample may additionally comprise other biological components, such as histologically appearing normal cells (e.g., adjacent to the prostate cancer), depending upon the method used to obtain the cancer tissue, such as surgical resection, biopsy, or bodily fluids.

"Recurrence", as used herein, refers to local or distant recurrence (i.e., metastasis) of cancer. For example, prostate cancer can recur locally in the tissue next to the prostate or in the seminal vesicles. The cancer may also affect the surrounding lymph nodes in the pelvis or lymph nodes outside this area. Prostate cancer can also spread to tissues next to the prostate, such as pelvic muscles, bones, or other organs. Recurrence can be determined by clinical recurrence detected by, e.g., imaging study or biopsy, or biochemical recurrence detected by, for example, sustained follow-up prostate-specific antigen (PSA) levels>0.4 ng/mL or the initiation of salvage therapy as a result of a rising PSA level.

"Reference population", "cohort", "cohort study", as used herein, are interchangeable and refer to a group of subjects with shared factors, influences or condition.

"Risk classification", as used herein, means a grouping of subjects by the level of risk (or likelihood) that the subject will experience a particular clinical outcome. A subject may be classified into a risk group or classified at a level of risk based on the methods of the present disclosure, e.g., high, medium or low risk. A "risk group" is a group of subjects or individuals with a similar level of risk for a particular clinical outcome.

"Sample", as used herein, refers to any biological material obtained via suitable methods known to the person skilled in the art from a subject. The sample may be collected in a clinically acceptable manner, e.g., in a way that cells, nucleic acids (such as DNA and RNA) and/or proteins are preserved. A "sample" may include body tissue and/or bodily fluids. Examples of bodily fluids include, but are not limited to, blood, plasma, serum, lymph, ascetic fluid, cystic fluid, urine, bile, nipple exudate, synovial fluid, bronchoalveolar lavage fluid, sputum, amniotic fluid, peritoneal fluid, cerebrospinal fluid, pleural fluid, pericardial fluid, semen, saliva, sweat and alveolar macrophages. In one embodiment of the invention, a "sample" may comprise a cell population derived from a glandular tissue, e.g., the sample may be derived from the prostate of a subject. In one embodiment, cells may be purified from obtained body tissues and/or bodily fluids if necessary, and then used as the "sample".

"Signature" or "molecular signature" are used interchangeably and refer to a group of markers whose combined expression levels is indicative of a biological condition, or of a particular prognosis or of a particular response of a subject to a treatment. In one embodiment, a signature refers to a group of at least 2 markers. In one embodiment, a signature refers to a group of at least 3, 4, 5, 6 or 7 markers. In one embodiment, a signature refers to a group of at least 8, 9, 10, 11, 12, 13, 14, 15 or 16 markers. In one embodiment, a signature refers to a group of at least 17, 18, 19, 20, 21, 22, 23, 24, 25, 26, 27, 28, 29, 30, 31, 32 or 33 markers.

In one embodiment, a signature refers to a group of at least 34, 35, 36, 37, 38 or 39 markers.

"Subject" refers to an animal, preferably a mammal, more preferably a human. In one embodiment, the subject is a patient, i.e. a recipient of health care services. Preferably, the subject is a cancer patient, i.e. he/she was previously diagnosed with cancer.

"Surgery", as used herein, applies to surgical methods undertaken for removal of cancerous tissue, including pelvic lymphadenectomy, radical prostatectomy, transurethral resection of the prostate (TURP), excision, dissection and tumor biopsy/removal. The prostate samples used for determining the expression levels of markers according to the present invention may have been obtained from any of these methods.

"Therapy", as used herein, includes radiation, hormonal therapy, cryosurgery, chemotherapy, biologic therapy, and high-intensity focused ultrasound.

"TMPRSS2/ERG fusion" as used herein refers to a fusion of the ERG oncogene to the androgen-driven 5'-TMPRSS2 gene, which has been demonstrated to have a significant association with prostate cancer (Tomlins et al., 2005. *Science.* 310(5748):644-8; Narod et al., 2008. Br J Cancer. 99(6):847-51). As used herein, positive TMPRSS/ERG fusion status (also termed "Fus+") indicates that the TMPRSS/ERG fusion is present in a tissue sample, whereas negative TMPRSS/ERG fusion status (also termed "Fus-") indicates that the TMPRSS/ERG fusion is not present in a tissue sample.

DETAILED DESCRIPTION

The present invention relates to molecular signatures of prostate cancer, wherein said molecular signatures comprise markers whose expression levels are different between indolent prostate cancer and aggressive prostate cancer. In other words, the present invention relates to molecular signatures of prostate cancer, wherein said molecular signatures are defined by the expression levels of markers, which are different between indolent prostate cancer and aggressive prostate cancer.

In one embodiment, the molecular signatures of the invention are specific of indolent prostate cancer. In one embodiment, the molecular signatures of the invention are specific of aggressive prostate cancer.

In one embodiment, the molecular signature of prostate cancer comprises or consists of at least one marker. In one embodiment, the molecular signature of prostate cancer comprises or consists of one marker. In one embodiment, the molecular signature of prostate cancer comprises or consists of at least 2 markers. In one embodiment, the molecular signature of prostate cancer comprises or consists of 2 markers. In one embodiment, the molecular signature of prostate cancer comprises or consists of at least 3, 4, 5 or 6 markers. In one embodiment, the molecular signature of prostate cancer comprises or consists of 3, 4, 5 or 6 markers. In one embodiment, the molecular signature of prostate cancer comprises or consists of at least 7 or 8 markers. In one embodiment, the molecular signature of prostate cancer comprises or consists of 7 or 8 markers. In one embodiment, the molecular signature of prostate cancer comprises or consists of at least 8, 9, 10, 11, 12, 13, 14 or 15 markers. In one embodiment, the molecular signature of prostate cancer comprises or consists of 8, 9, 10, 11, 12, 13, 14 or 15 markers. In one embodiment, the molecular signature of prostate cancer comprises or consists of at least 10, 11, 12, 13, 14, 15, 16, 17 or 18 markers. In one embodiment, the molecular signature of prostate cancer comprises or consists of 10, 11, 12, 13, 14, 15, 16, 17 or 18 markers. In one embodiment, the molecular signature according to the present invention comprises or consists of at least 17, 18, 19, 20, 21, 22, 23, 24, 25, 26, 27, 28, 29, 30, 31, 32 or 33 markers. In one embodiment, the molecular signature according to the present invention comprises or consists of 17, 18, 19, 20, 21, 22, 23, 24, 25, 26, 27, 28, 29, 30, 31, 32 or 33 markers. In one embodiment, the molecular signature according to the present invention comprises or consists of at least 34, 35, 36, 37, 38 or 39 markers. In one embodiment, the molecular signature according to the present invention comprises or consists of 34, 35, 36, 37, 38 or 39 markers. In one embodiment, the molecular signature according to the present invention comprises or consists of at least 34, 35, 36, 37, 38, 39 or 40 markers. In one embodiment, the molecular signature according to the present invention comprises or consists of 34, 35, 36, 37, 38, 39 or 40 markers. In one embodiment, the molecular signature according to the present invention comprises or consists of at least 39 markers. In one embodiment, the molecular signature according to the present invention comprises or consists of 39 markers. In one embodiment, the molecular signature according to the present invention comprises or consists of 40 markers. In one embodiment, the molecular signature according to the present invention comprises at least 40 markers.

The present application thus also relates to one or several marker(s) whose expression level is/are different between indolent prostate cancers and aggressive prostate cancers. A marker whose expression is different between indolent prostate cancers and aggressive prostate cancers will be hereinafter referred to as a "prostate cancer marker".

Methods for determining prostate cancer markers are well-known from the skilled artisan, and include, without limitation, comparing the transcriptome (in an embodiment wherein expression relates to transcription of a marker) or proteome (in an embodiment wherein expression relates to translation of a marker) in a sample from subjects with known recurrence outcome.

In one embodiment of the invention, a marker is considered as differentially expressed in conditions of indolent prostate cancers and aggressive prostate cancers if, according to a t-test, the p-value after false discovery rate (FDR) correction is lower than 0.05, preferably lower than 0.01.

In one embodiment, prostate cancer markers are selected from a list of 2 prostate cancer markers comprising or consisting of CD38 and COMP. Therefore, the present invention also relates to a set of 2 prostate cancer markers. Accordingly, the present invention also relates to a set of 2 prostate cancer markers comprising or consisting of CD38 and COMP.

In another embodiment, prostate cancer markers are selected from a list of 6 prostate cancer markers comprising or consisting of ANPEP, AZGP1, CHRNA2, COMP, KHDRBS3 and SFRP4. Therefore, the present invention also relates to a set of 6 prostate cancer markers. Accordingly, the present invention also relates to a set of 6 prostate cancer markers comprising or consisting of ANPEP, AZGP1, CHRNA2, COMP, KHDRBS3 and SFRP4.

In another embodiment, prostate cancer markers are selected from a list of 7 prostate cancer markers comprising or consisting of ASPN, CD38, COL10A1, COMP, CXCL14, NCAPD3 and SFRP4. Therefore, the present invention also relates to a set of 7 prostate cancer markers. Accordingly, the present invention also relates to a set of 7 prostate cancer markers comprising or consisting of ASPN, CD38, COL10A1, COMP, CXCL14, NCAPD3 and SFRP4.

In another embodiment, prostate cancer markers are selected from a list of 8 prostate cancer markers comprising or consisting of ANPEP, ANTXR1, AZGP1, CHRNA2, COMP, KHDRBS3, MS4A6A and SFRP4. Therefore, the present invention also relates to a set of 8 prostate cancer markers. Accordingly, the present invention also relates to a set of 8 prostate cancer markers comprising or consisting of ANPEP, ANTXR1, AZGP1, CHRNA2, COMP, KHDRBS3, MS4A6A and SFRP4.

In another embodiment, prostate cancer markers are selected from a list of 15 prostate cancer markers comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN. Therefore, the present invention also relates to a set of 15 prostate cancer markers. Accordingly, the present invention also relates to a set of 15 prostate cancer markers comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In another embodiment, prostate cancer markers are selected from a list of 16 prostate cancer markers comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN. Therefore, the present invention also relates to a set of 16 prostate cancer markers. Accordingly, the present invention also relates to a set of 16 prostate cancer markers comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN.

In another embodiment, prostate cancer markers are selected from a list of 16 prostate cancer markers comprising or consisting of AFF3, ANTXR1, CHRNA2, COL1A2, COL3A1, FAM3B, FMOD, FRZB, GPT2, HGD, KHDRBS3, MS4A6A, NCAPD3, SLC15A2, SLC22A3 and STXBP6. Therefore, the present invention also relates to a set of 16 prostate cancer markers. Accordingly, the present invention also relates to a set of 16 prostate cancer markers comprising or consisting of AFF3, ANTXR1, CHRNA2, COL1A2, COL3A1, FAM3B, FMOD, FRZB, GPT2, HGD, KHDRBS3, MS4A6A, NCAPD3, SLC15A2, SLC22A3 and STXBP6.

In another embodiment, prostate cancer markers are selected from a list of 18 prostate cancer markers comprising or consisting of ACADL, ANPEP, ANTXR1, AZGP1, CHRNA2, COL1A1, COL3A, COMP, FMOD, GPT2, ITGBL1, KHDRBS3, NCAPD3, REPS2, SFRP4, SLC15A2, SLC22A3 and SPARC. Therefore, the present invention also relates to a set of 18 prostate cancer markers. Accordingly, the present invention also relates to a set of 18 prostate cancer markers comprising or consisting of ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In another embodiment, prostate cancer markers are selected from a list of 33 prostate cancer markers comprising or consisting of ACADL, AFF3, ANO7, ANPEP, ASPN, AZGP1, CD38, CHRNA2, COL1A1, COL1A2, COL3A1, COL8A1, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN. Therefore, the present invention also relates to a set of 33 prostate cancer markers. Accordingly, the present invention also relates to a set of 33 prostate cancer markers comprising or consisting of ACADL, AFF3, ANO7, ANPEP, ASPN, AZGP1, CD38, CHRNA2, COL1A1, COL1A2, COL3A1, COL8A1, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN.

In another embodiment, prostate cancer markers are selected from a list of 39 prostate cancer markers comprising or consisting of ACADL, AFF3, ANO7, ANPEP, ANTXR1, ASPN, AZGP1, CD38, CDH1, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN. Therefore, the present invention also relates to a set of 39 prostate cancer markers. Accordingly, the present invention also relates to a set of 39 prostate cancer markers comprising or consisting of ACADL, AFF3, ANO7, ANPEP, ANTXR1, ASPN, AZGP1, CD38, CDH1, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In another embodiment, prostate cancer markers are selected from a list of 40 prostate cancer markers comprising or consisting of ACADL, AFF3, ANO7, ANPEP, ANTXR1, ASPN, AZGP1, CD38, CDH1, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2, TMPRSS/ERG and VCAN. Therefore, the present invention also relates to a set of 40 prostate cancer markers. Accordingly, the present invention also relates to a set of 40 prostate cancer markers comprising or consisting of ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2, TMPRSS/ERG and VCAN.

As used herein, "ACADL" refers to a gene coding for acyl-CoA dehydrogenase long chain, with Entrez Gene ID No 33.

As used herein, "AFF3" refers to a gene coding for AF4/FMR2 family member 3, with Entrez Gene ID No 3899.

As used herein, "ANO7" refers to a gene coding for anoctamin 7, with Entrez Gene ID No 50636.

As used herein, "ANPEP" refers to a gene coding for alanyl aminopeptidase, with Entrez Gene ID No 290.

As used herein, "ANTXR1" refers to a gene coding for anthrax toxin receptor 1, with Entrez Gene ID No 84168.

As used herein, "ASPN" refers to a gene coding for asporin, with Entrez Gene ID No 54829.

As used herein, "AZGP1" refers to a gene coding for α-2-glycoprotein 1, with Entrez Gene ID No 563.

As used herein, "CD38" refers to a gene coding for CD38, with Entrez Gene ID No 952.

As used herein, "CDH11" refers to a gene coding for cadherin 11, with Entrez Gene ID No 1009.

As used herein, "CHRNA2" refers to a gene coding for cholinergic receptor nicotinic α2 subunit, with Entrez Gene ID No 1135.

As used herein, "COL1A1" refers to a gene coding for collagen type I α1 chain, with Entrez Gene ID No 1277.

As used herein, "COL1A2" refers to a gene coding for collagen type I α2 chain, with Entrez Gene ID No 1278.

As used herein, "COL3A1" refers to a gene coding for collagen type III α1 chain, with Entrez Gene ID No 1281.

As used herein, "COL8A1" refers to a gene coding for collagen type VIII α1 chain, with Entrez Gene ID No 1295.

As used herein, "COL10A" refers to a gene coding for collagen type X α1 chain, with Entrez Gene ID No 1300.

As used herein, "COMP" refers to a gene coding for cartilage oligomeric matrix protein, with Entrez Gene ID No 1311.

As used herein, "CPXM2" refers to a gene coding for carboxypeptidase X, M14 family member 2, with Entrez Gene ID No 119587.

As used herein, "CXCL14" refers to a gene coding for C-X-C motif chemokine ligand 14, with Entrez Gene ID No 9547.

As used herein, "FAM3B" refers to a gene coding for family with sequence similarity 3 member B, with Entrez Gene ID No 54097.

As used herein, "FMOD" refers to a gene coding for fibromodulin, with Entrez Gene ID No 2331.

As used herein, "FRZB" refers to a gene coding for frizzled related protein, with Entrez Gene ID No 2487.

As used herein, "GPT2" refers to a gene coding for glutamic-pyruvic transaminase 2, with Entrez Gene ID No 84706.

As used herein, "HGD" refers to a gene coding for homogentisate 1,2-dioxygenase, with Entrez Gene ID No 3081.

As used herein, "ITGBL1" refers to a gene coding for integrin subunit β like 1, with Entrez Gene ID No 9358.

As used herein, "KHDRBS3" refers to a gene coding for KH RNA binding domain containing, signal transduction associated 3, with Entrez Gene ID No 10656.

As used herein, "MGP" refers to a gene coding for matrix Gla protein, with Entrez Gene ID No 4256.

As used herein, "MS4A6A" refers to a gene coding for membrane spanning 4-domains A6A, with Entrez Gene ID No 64231.

As used herein, "NCAPD3" refers to a gene coding for non-SMC condensin II complex subunit D3, with Entrez Gene ID No 23310.

As used herein, "NOX4" refers to a gene coding for NADPH oxidase 4, with Entrez Gene ID No 50507.

As used herein, "REPS2" refers to a gene coding for RALBP1 associated Eps domain containing 2, with Entrez Gene ID No 9185.

As used herein, "SFRP2" refers to a gene coding for secreted frizzled related protein 2, with Entrez Gene ID No 6423.

As used herein, "SFRP4" refers to a gene coding for secreted frizzled related protein 4, with Entrez Gene ID No 6424.

As used herein, "SLC15A2" refers to a gene coding for solute carrier family 15 member 2, with Entrez Gene ID No 6565.

As used herein, "SLC22A3" refers to a gene coding for solute carrier family 22 member 3, with Entrez Gene ID No 6581.

As used herein, "SPARC" refers to a gene coding for secreted protein acidic and cysteine rich, with Entrez Gene ID No 6678.

As used herein, "STXBP6" refers to a gene coding for syntaxin binding protein 6, with Entrez Gene ID No 29091.

As used herein, "SULF1" refers to a gene coding for sulfatase 1, with Entrez Gene ID No 23213.

As used herein, "THBS2" refers to a gene coding for thrombospondin 2, with Entrez Gene ID No 7058.

As used herein, "VCAN" refers to a gene coding for versican, with Entrez Gene ID No 1462.

As use herein, "TMPRSS/ERG" refers to a fusion of the androgen-driven TMPRSS2 gene (with Entrez Gene ID No 7113) with the ERG oncogene (with Entrez Gene ID No 2078).

In one embodiment, the molecular signature according to the present invention comprises or consists of at least 1 prostate cancer marker, preferably at least 2 markers selected from the group comprising or consisting of CD38 and COMP.

In one embodiment, the signature comprises or consists of at least 1 prostate cancer marker, preferably at least 2, 3, 4, 5 or 6 prostate cancer markers selected from the group comprising or consisting of ANPEP, AZGP1, CHRNA2, COMP, KHDRBS3 and SFRP4.

In one embodiment, the signature comprises or consists of at least 1 prostate cancer marker, preferably at least 2, 3, 4, 5, 6 or 7 prostate cancer markers selected from the group comprising or consisting of ASPN, CD38, COL10A1, COMP, CXCL14, NCAPD3 and SFRP4.

In one embodiment, the signature comprises or consists of at least 1 prostate cancer marker, preferably at least 2, 3, 4, 5, 6, 7 or 8 prostate cancer markers selected from the group comprising or consisting of ANPEP, ANTXR1, AZGP1, CHRNA2, COMP, KHDRBS3, MS4A6A and SFRP4.

In one embodiment, the signature comprises or consists of at least 1 prostate cancer marker, preferably at least 2, 3, 4, 5, 6, 7, 8, 9, 10, 11, 12, 13, 14 or 15 prostate cancer markers selected from the group comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In one embodiment, the signature comprises or consists of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN.

In one embodiment, the signature comprises or consists of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ANTXR1, CHRNA2, COL1A2, COL3A, FAM3B, FMOD, FRZB, GPT2, HGD, KHDRBS3, MS4A6A, NCAPD3, SLC15A2, SLC22A3 and STXBP6.

In one embodiment, the signature comprises or consists of at least 1 prostate cancer marker, preferably at least 2, 3, 4, 5, 6, 7, 8, 9, 10, 11, 12, 13, 14, 15, 16, 17 or 18 prostate cancer markers selected from the group comprising or consisting of ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In one embodiment, the signature comprises or consists of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 prostate cancer markers selected from the group comprising or consisting of ACADL, AFF3, ANO7, ANPEP, ASPN, AZGP1, CD38, CHRNA2, COL1A1, COL1A2, COL3A1, COL8A, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN.

In one embodiment, the signature comprises or consists of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers selected from the group comprising or consisting of ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In one embodiment, the signature comprises or consists of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 prostate cancer markers selected from the group comprising or consisting of ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2, TMPRSS/ERG and VCAN.

In one embodiment, the signature according to the present invention is indicative of indolent prostate cancer and is characterized by the expression levels of at least 1 prostate cancer marker, preferably at least 2 prostate cancer markers selected from the group comprising or consisting of CD38 and COMP, with:
  COMP being underexpressed, and
  CD38 being overexpressed.

In one embodiment, the signature according to the present invention is indicative of indolent prostate cancer and is characterized by the expression levels of at least 1 prostate cancer marker, preferably at least 2, 3, 4, 5 or 6 prostate cancer markers selected from the group comprising or consisting of ANPEP, AZGP1, CHRNA2, COMP, KHDRBS3 and SFRP4, with:
  COMP, KHDRBS3 and SFRP4 being underexpressed, and
  ANPEP, AZGP1 and CHRNA2 being overexpressed.

In one embodiment, the signature according to the present invention is indicative of indolent prostate cancer and is characterized by the expression levels of at least 1 prostate cancer marker, preferably at least 2, 3, 4, 5, 6 or 7 prostate cancer markers selected from the group comprising or consisting of ASPN, CD38, COL10A1, COMP, CXCL14, NCAPD3 and SFRP4, with:
  ASPN, COL10A1, COMP, CXCL14 and SFRP4 being underexpressed, and
  CD38 and NCAPD3 being overexpressed.

In one embodiment, the signature according to the present invention is indicative of indolent prostate cancer and is characterized by the expression levels of at least 1 prostate cancer marker, preferably at least 2, 3, 4, 5, 6, 7 or 8 prostate cancer markers selected from the group comprising or consisting of ANPEP, ANTXR1, AZGP1, CHRNA2, COMP, KHDRBS3, MS4A6A and SFRP4, with:
  ANTXR1, COMP, KHDRBS3, MS4A6A and SFRP4 being underexpressed, and
  ANPEP, AZGP1 and CHRNA2 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14 or 15 prostate cancer markers selected from the group comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN, with:
  COL1A1, COMP, KHDRBS3, SFRP4 and VCAN being underexpressed, and
  ACADL, ANPEP, AZGP1, CHRNA2, FMOD, GPT2, NCAPD3, REPS2, SLC15A2 and SLC22A3 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN, with:
  ASPN, COL10A1, COMP, CXCL14, KHDRBS3, SFRP2, SFRP4 and VCAN being underexpressed, and
  AFF3, AZGP1, CD38, CHRNA2, FMOD, NCAPD3, SLC15A2 and SLC22A3 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ANTXR1, CHRNA2, COL1A2, COL3A, FAM3B, FMOD, FRZB, GPT2, HGD, KHDRBS3, MS4A6A, NCAPD3, SLC15A2, SLC22A3 and STXBP6, with:
  ANTXR1, COL1A2, COL3A1, FRZB, KHDRBS3 and MS4A6A being underexpressed, and
  AFF3, CHRNA2, FAM3B, FMOD, GPT2, HGD, NCAPD3, SLC15A2, SLC22A3 and STXBP6 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14, 15, 16, 17 or 18 prostate cancer markers selected from the group comprising or consisting of ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC, with:
  ANTXR1, COL1A1, COL3A1, COMP, ITGBL1, KHDRBS3, SFRP4 and SPARC being underexpressed, and
  ACADL, ANPEP, AZGP1, CHRNA2, FMOD, GPT2, NCAPD3, REPS2, SLC15A2 and SLC22A3 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 prostate cancer markers selected from the group comprising or consisting of ACADL, AFF3, ANO7, ANPEP, ASPN, AZGP1, CD38, CHRNA2, COL1A1, COL1A2, COL3A1, COL8A, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN, with:
ASPN, COL1A1, COL1A2, COL3A1, COL8A1, COL10A1, COMP, CPXM2, CXCL14, FRZB, KHDRBS3, MGP, NOX4, SFRP2, SFRP4, SULF1, THBS2 and VCAN being underexpressed, and
ACADL, AFF3, ANO7, ANPEP, AZGP1, CD38, CHRNA2, FAM3B, FMOD, GPT2, HGD, NCAPD3, REPS2, SLC15A2 and SLC22A3 being overexpressed.

In one embodiment, the signature according to the present invention is indicative of indolent prostate cancer and is characterized by the expression levels of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers selected from the group comprising or consisting of ACADL, AFF3, ANO7, ANPEP, ANTXR1, ASPN, AZGP1, CD38, CDH11, CHRNA2, COL1A1, COL1A2, COL3A1, COL8A1, COL10A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN, with:
ANTXR1, ASPN, CDH11, COL1A1, COL1A2, COL3A1, COL8A1, COL10A1, COMP, CPXM2, CXCL14, FRZB, ITGBL1, KHDRBS3, MGP, MS4A6A, NOX4, SFRP2, SFRP4, SPARC, SULF1, THBS2 and VCAN being underexpressed, and
ACADL, AFF3, ANO7, ANPEP, AZGP1, CD38, CHRNA2, FAM3B, FMOD, GPT2, HGD, NCAPD3, REPS2, SLC15A2, SLC22A3 and STXBP6 being overexpressed.

In a preferred embodiment, the signature according to the present invention is indicative of TMPRSS/ERG fusion positive indolent prostate cancer. In a preferred embodiment, the signature according to the present invention is not indicative of TMPRSS/ERG fusion negative indolent prostate cancer.

In one embodiment, the signature according to the present invention is indicative of aggressive prostate cancer and is characterized by the expression levels of at least 1 prostate cancer marker, preferably at least 2 prostate cancer markers selected from the group comprising or consisting of CD38 and COMP, with:
COMP being overexpressed, and
CD38 being underexpressed.

In one embodiment, the signature according to the present invention is indicative of aggressive prostate cancer and is characterized by the expression levels of at least 1 prostate cancer marker, preferably at least 2, 3, 4, 5 or 6 prostate cancer markers selected from the group comprising or consisting of ANPEP, AZGP1, CHRNA2, COMP, KHDRBS3 and SFRP4, with:
COMP, KHDRBS3 and SFRP4 being overexpressed, and
ANPEP, AZGP1 and CHRNA2 being underexpressed.

In one embodiment, the signature according to the present invention is indicative of aggressive prostate cancer and is characterized by the expression levels of at least 1 prostate cancer marker, preferably at least 2, 3, 4, 5, 6 or 7 prostate cancer markers selected from the group comprising or consisting of ASPN, CD38, COL10A1, COMP, CXCL14, NCAPD3 and SFRP4, with:
ASPN, COL10A1, COMP, CXCL14 and SFRP4 being overexpressed, and
CD38 and NCAPD3 being underexpressed.

In one embodiment, the signature according to the present invention is indicative of aggressive prostate cancer and is characterized by the expression levels of at least 1 prostate cancer marker, preferably at least 2, 3, 4, 5, 6, 7 or 8 prostate cancer markers selected from the group comprising or consisting of ANPEP, ANTXR1, AZGP1, CHRNA2, COMP, KHDRBS3, MS4A6A and SFRP4, with:
ANTXR1, COMP, KHDRBS3, MS4A6A and SFRP4 being overexpressed, and
ANPEP, AZGP1 and CHRNA2 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14 or 15 prostate cancer markers selected from the group comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN, with:
COL1A1, COMP, KHDRBS3, SFRP4 and VCAN being overexpressed, and
ACADL, ANPEP, AZGP1, CHRNA2, FMOD, GPT2, NCAPD3, REPS2, SLC15A2 and SLC22A3 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN, with:
ASPN, COL10A1, COMP, CXCL14, KHDRBS3, SFRP2, SFRP4 and VCAN being overexpressed, and
AFF3, AZGP1, CD38, CHRNA2, FMOD, NCAPD3, SLC15A2 and SLC22A3 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14, 15 or 16 prostate cancer markers selected from the group comprising or consisting of AFF3, ANTXR1, CHRNA2, COL1A2, COL3A, FAM3B, FMOD, FRZB, GPT2, HGD, KHDRBS3, MS4A6A, NCAPD3, SLC15A2, SLC22A3 and STXBP6, with:
ANTXR1, COL1A2, COL3A1, FRZB, KHDRBS3 and MS4A6A being overexpressed, and
AFF3, CHRNA2, FAM3B, FMOD, GPT2, HGD, NCAPD3, SLC15A2, SLC22A3 and STXBP6 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14, 15, 16, 17 or 18 prostate cancer markers selected from the group comprising or consisting of ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC, with:
ANTXR1, COL1A1, COL3A, COMP, ITGBL1, KHDRBS3, SFRP4 and SPARC being overexpressed, and ACADL, ANPEP, AZGP1, CHRNA2, FMOD, GPT2, NCAPD3, REPS2, SLC15A2 and SLC22A3 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 prostate cancer markers selected from the group comprising or consisting of ACADL, AFF3, ANO7, ANPEP, ASPN, AZGP1, CD38, CHRNA2, COL1A1, COL1A2, COL3A1, COL8A, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN, with:
ASPN, COL1A1, COL1A2, COL3A1, COL8A1, COL10A1, COMP, CPXM2, CXCL14, FRZB, KHDRBS3, MGP, NOX4, SFRP2, SFRP4, SULF1, THBS2 and VCAN being overexpressed, and
ACADL, AFF3, ANO7, ANPEP, AZGP1, CD38, CHRNA2, FAM3B, FMOD, GPT2, HGD, NCAPD3, REPS2, SLC15A2 and SLC22A3 being underexpressed.

In one embodiment, the signature according to the present invention is indicative of aggressive prostate cancer and is characterized by the expression levels of at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers selected from the group comprising or consisting of ACADL, AFF3, ANO7, ANPEP, ANTXR1, ASPN, AZGP1, CD38, CDH11, CHRNA2, COL1A1, COL1A2, COL3A1, COL8A1, COL10A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN, with:
ANTXR1, ASPN, CDH11, COL1A1, COL1A2, COL3A1, COL8A1, COL10A1, COMP, CPXM2, CXCL14, FRZB, ITGBL1, KHDRBS3, MGP, MS4A6A, NOX4, SFRP2, SFRP4, SPARC, SULF1, THBS2 and VCAN being overexpressed, and
ACADL, AFF3, ANO7, ANPEP, AZGP1, CD38, CHRNA2, FAM3B, FMOD, GPT2, HGD, NCAPD3, REPS2, SLC15A2, SLC22A3 and STXBP6 being underexpressed.

In a preferred embodiment, the signature according to the present invention is indicative of TMPRSS/ERG fusion positive (Fus$^+$) aggressive prostate cancer. In a preferred embodiment, the signature according to the present invention is not indicative of TMPRSS/ERG fusion negative (Fus$^-$) aggressive prostate cancer.

The molecular signatures of the present invention were identified by computer-implemented, algorithm-based approaches after it had been shown that two discrete disease specific states, i.e., indolent and aggressive, exist in the case of TMPRSS/ERG fusion positive (Fus$^+$) prostate cancer. With this knowledge at hand, it was speculated that computer-implemented, algorithm-based approaches can be used to identify such signature in existing expression data. Such an approach is described in the Example section of the present application.

In one embodiment, the expression level of the prostate cancer markers of the invention corresponds to their transcription levels (i.e., the expression of the mRNA) or to their translation levels (i.e., expression of the protein) of the prostate cancer markers.

In one embodiment, the expression level of the prostate cancer markers is assessed at the protein level, i.e., at the translation level. Methods for determining a protein level in a sample are well-known in the art. Examples of such methods include, but are not limited to, immunohistochemistry, multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA) and the like.

In one embodiment, the expression level of the prostate cancer markers is assessed at the RNA level i.e., at the transcription level. Methods for assessing the transcription level of a marker are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "whole transcriptome shotgun sequencing") and the like.

In one embodiment, the decision as to whether a certain prostate cancer marker in a specific sample is overexpressed or underexpressed is taken in comparison to a reference signature. This reference signature may be either implemented in the software or an overall median or other arithmetic mean across measurements may be built.

In one embodiment, the reference signature can be relative to a signature derived from population studies, including without limitation, such subjects having similar age range, subjects in the same or similar ethnic group, similar cancer history and the like.

In one embodiment, the reference signature is derived from the measurement of the expression levels of prostate cancer markers according to the invention, in a control sample derived from one or more substantially healthy subjects. As used herein, a "substantially healthy subject" has not been previously diagnosed or identified as having or suffering from prostate cancer.

In one embodiment, the reference signature is derived from the measurement of the expression levels of prostate cancer markers according to the invention, in a reference sample derived from a healthy tissue or sample of the same subject, whereas the molecular signature to be compared is measured in a sample taken from a suspect mass of cells (i.e., from the suspected tumor) within the body of the subject.

In one embodiment, the reference signature is derived from the previous measurement of the expression levels of prostate cancer markers according to the invention, in a reference sample derived from the same subject, such as, for example, the expression profile measured one month before, preferably six months before, more preferably one year before or more.

In a preferred embodiment, the reference signature is derived from the measurement of the expression levels of prostate cancer markers according to the invention, in a reference population.

In one embodiment, the reference population comprises substantially healthy subjects, preferably at least 50, more preferably at least 100, more preferably at least 200 and even more preferably at least 500 substantially healthy subjects.

In a preferred embodiment, the reference population comprises subjects diagnosed with prostate cancer, preferably at least 100, more preferably at least 250, more preferably at least 500 subjects diagnosed with prostate cancer.

In a still preferred embodiment, the reference population comprises subjects diagnosed with prostate cancer, preferably at least 100, more preferably at least 250, more preferably at least 500 subjects diagnosed with prostate cancer and of known outcome, i.e., of known prostate cancer recurrence status.

In a still preferred embodiment, the reference population comprises subjects diagnosed with prostate cancer, preferably at least 100, more preferably at least 250, more preferably at least 500 subjects diagnosed with indolent prostate cancer.

In a still preferred embodiment, the reference population comprises subjects diagnosed with prostate cancer, preferably at least 100, more preferably at least 250, more preferably at least 500 subjects diagnosed with aggressive prostate cancer.

By implying a multitude of samples from the reference population, it is conceivable to calculate a median and/or mean expression level for each gene respectively. In relation to these results, a respective gene expression value can be monitored as overexpressed or underexpressed. In one embodiment, the reference signature corresponds to the mean expression levels of the prostate cancer markers of the signature of the invention, measured in the reference population. In one embodiment, the reference signature corresponds to the median expression levels of the prostate cancer markers of the signature of the invention, measured in the reference population.

In one embodiment, the reference signature is constructed using algorithms and other methods of statistical and structural classification. Samples from the reference population are used to compute a mean profile on the at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers according to the invention. These mean profiles are computed for three reference groups of (1) low risk PCa, (2) high risk PCa, and (3) normal adjacent tissues, and thereafter referred to as "group centroids". In one embodiment, the centroids are centered. In one embodiment, the centroids are scaled by prostate cancer marker. In one embodiment, the centroids are centered and scaled by prostate cancer marker. Cancer class prediction from gene expression profiling based on a centroid classification is a technic well-known from the one skilled in the art. Reference can be made, e.g., to Tibshirani et al., 2002. *Proc Nat Acad Sci USA*. 99(10): 6567-72; Dabney, 2005. *Bioinformatics*. 21(22):4148-54; and Shen et al., 2009. *J Biomed Inform*. 42(1):59-65.

In one embodiment, a new subject will be assigned to low risk, high risk, or undefined if the profile of a sample from said subject has the highest correlation with the low risk, high risk or undefined centroid, respectively.

The present invention also relates to a method for predicting the risk of prostate cancer recurrence in a subject affected with prostate cancer, using the molecular signatures of the invention.

The present invention also relates to a method for discriminating between indolent prostate cancer and aggressive prostate cancer in a subject affected with prostate cancer, using the molecular signatures of the invention.

The present invention also relates to a method for prognosticating the progress of prostate cancer in a subject, using the molecular signatures of the invention.

The present invention also relates to a method for diagnosing indolent prostate cancer in a subject affected with prostate cancer, using the molecular signatures of the invention.

The present invention also relates to a method for determining a personalized course of treatment in a subject affected with prostate cancer, using the molecular signatures of the invention.

In one embodiment, the methods of the invention comprise a step of determining a molecular signature according to the present invention, in a sample of the subject.

The term "sample" as used herein generally refers to any sample which may be tested for expression levels of a marker, preferably of prostate cancer markers according to the present invention.

In one embodiment, the methods of the invention comprise a step of providing a sample from the subject.

In one embodiment, the sample is a body tissue sample. Examples of body tissues include, but are not limited to, prostate, muscle, nerve, brain, heart, lung, liver, pancreas, spleen, thymus, esophagus, stomach, intestine, kidney, testis, ovary, hair, skin, bone, breast, uterus, bladder and spinal cord.

In one embodiment, the sample is a prostate tissue sample. Therefore, according to this embodiment, the methods of the invention comprise a step of providing a prostate tissue sample from the subject.

In one embodiment, the sample is a biopsy sample, preferably a prostate biopsy sample, more preferably a prostate cancer biopsy sample. In one embodiment, the sample is a fine-needle aspirate sample, preferably a prostate fine-needle aspirate sample, more preferably a prostate cancer fine-needle aspirate sample. In one embodiment, the sample is a resection sample, preferably a prostate resection sample, more preferably a prostate cancer resection sample. As used herein, the term "prostatectomy" is used to define the removal of all or part of the prostate. Therefore, in one embodiment, the sample is a prostate tissue sample after prostatectomy.

In one embodiment, the sample is a bodily fluid. Examples of bodily fluids include, but are not limited to, blood, plasma, serum, lymph, ascetic fluid, cystic fluid, urine, bile, nipple exudate, synovial fluid, bronchoalveolar lavage fluid, sputum, amniotic fluid, peritoneal fluid, cerebrospinal fluid, pleural fluid, pericardial fluid, semen, saliva, sweat and alveolar macrophages.

In one embodiment, the sample was previously taken from the subject, i.e., the methods of the invention do not comprise a step of recovering a sample from the subject. Consequently, according to this embodiment, the methods of the invention are non-invasive methods.

In one embodiment, the methods of the invention comprise a step of determining the TMPRSS/ERG fusion status of said sample from the subject.

The one skilled in the art is familiar with means and methods to determine the TMPRSS/ERG fusion status in a sample. These include the use of rt-PCR, qPCR or high-throughput sequencing (Mertz et al., 2007. *Neoplasia*. 9(3): 200-206; Maher et al., 2009. *Nature*. 458(7234):97-101). More recently, diagnosis tests have been developed for rapid and cost-effective determination of the TMPRSS/ERG status, including, but not limited to, immunohistochemistry tests (Chaux et al., 2011. *Am J Surg Pathol*. 35(7):1014-20) and urine-based test (Koo et al., 2016. *Sci Rep*. 6:30722).

In one embodiment, the methods of the invention comprise a step of determining the molecular signature according to the present invention of said sample from the subject.

In one embodiment, the step of determining the molecular signature according to the present invention of said sample from the subject is performed only if the TMPRSS/ERG fusion status of the sample showed positive (Fus⁺).

In one embodiment, the step of determining the molecular signature comprises a substep of extracting total RNA from the sample.

In one embodiment, the step of determining the molecular signature comprises a substep of retro-transcribing total RNA extracted from the sample, thereby obtaining total cDNA.

In one embodiment, the step of determining the molecular signature comprises a substep of amplifying by PCR, preferably by qPCR, the cDNA corresponding to at least one prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers according to the present invention, such as, e.g., 8, 15, 18 or 39 prostate cancer markers as described hereinabove.

In one embodiment, the step of determining the molecular signature comprises a substep of measuring the expression level of at least one prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers according to the present invention, such as, e.g., 8, 15, 18 or 39 prostate cancer markers as described hereinabove.

In one embodiment, the expression level of the at least one prostate cancer marker, preferably of the at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers, is measured using a DNA microarray, so that the expression levels of each of the prostate cancer markers of the molecular signature of the invention are simultaneously measured.

In one embodiment, the expression level of the at least one prostate cancer marker, preferably of the at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers, is measured using RNAseq.

In one embodiment, the expression level of the at least one prostate cancer marker, preferably of the at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers, is measured using a CodeSet. Custom CodeSets for a given panel of markers (e.g., for the prostate cancer markers disclosed herein) are commercially designable. These include, without limitation, nCounter© Custom CodeSets (NanoString) (Malkov et al., 2009. *BMC Res Notes*. 2:80; Kulkarni, 2011. *Curr Protoc Mol Biol*. Chapter 25:Unit25B.10).

In one embodiment, the methods of the invention comprise a step of comparing the molecular signature determined from the sample of the subject, with a reference signature.

The reference signature may be either implemented in the software or an overall median or other arithmetic mean across measurements may be built.

In one embodiment, the reference signature is relative to a signature derived from population studies, including without limitation, such subjects having similar age range, subjects in the same or similar ethnic group, similar cancer history and the like.

In one embodiment, the reference signature is derived from the measurement of the expression levels of prostate cancer markers according to the invention, in a reference population.

In one embodiment, the reference population comprises subjects diagnosed with prostate cancer, preferably at least 100, more preferably at least 250, even more preferably at least 500 subjects diagnosed with prostate cancer.

In a preferred embodiment, the reference population comprises subjects diagnosed with prostate cancer, preferably at least 100, more preferably at least 250, even more preferably at least 500 subjects diagnosed with prostate cancer and of known outcome, i.e., of known prostate cancer recurrence status.

In a still preferred embodiment, the reference population comprises subjects diagnosed with prostate cancer, preferably at least 100, more preferably at least 250, even more preferably at least 500 subjects diagnosed with indolent prostate cancer.

By implying a multitude of samples from the reference population, it is conceivable to calculate a median and/or mean expression level for each prostate cancer marker respectively. In relation to these results, a respective prostate cancer marker expression value can be monitored as upregulated (or overexpressed) or downregulated (or underexpressed). In one embodiment, the reference signature corresponds to the mean expression levels of the prostate cancer markers of the signature of the invention, measured in the reference population. In one embodiment, the reference signature corresponds to the median expression levels of the prostate cancer markers of the signature of the invention, measured in the reference population.

In one embodiment, the reference signature is constructed using algorithms and other methods of statistical and structural classification. In a preferred embodiment, the reference signature corresponds to a computation of a mean profile on the at least 1 prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 prostate cancer markers according to the invention (such as, e.g., 8, 15, 18 or 39 prostate cancer markers as described hereinabove) in samples from the reference population. These mean profiles are computed for three reference groups of (1) low risk PCa, (2) high risk PCa, and (3) normal adjacent tissues, and referred to as "group centroids". The centroids may be centered and/or scaled by prostate cancer marker.

In one embodiment, a prostate cancer marker is considered as differentially expressed (i.e., overexpressed or underexpressed) in the sample from the subject as compared to the reference signature if both expression levels differ by a factor of at least 1.1, preferably of at least 1.5, more preferably of at least 2 and even more preferably of at least 5.

In one embodiment, the methods of the invention comprise a step of assigning the subject to a risk group based on the correlation of the molecular signature with the reference signature.

In one embodiment, the subject may be assigned to a low recurrence risk group. As used herein, the term "low recurrence risk group" or "low risk group" refers to a group of subjects whose prostate cancer is not likely to evolve to a higher stage of the disease, i.e., these subjects are diagnosed with a low recurrence risk prostate cancer (also termed indolent prostate cancer, biochemical recurrence-free prostate cancer or non-relapsing prostate cancer).

In one embodiment, a "low recurrence risk" means that a subject is expected to have no distant metastases of prostate cancer within 2, preferably 3, 5, 8 or 10 years. In one embodiment, a "low recurrence risk" means that a subject is expected to have no biochemical recurrence of prostate cancer within 2, preferably 3, 5, 8 or 10 years. In one embodiment, a "low recurrence risk" means that a subject is expected to have no relapse of prostate cancer within 2, preferably 3, 5, 8 or 10 years.

In one embodiment, the subject may be assigned to a high recurrence risk group. As used herein, the term "high recurrence risk group" or "high risk group" refers to a group of subjects whose prostate cancer is likely to evolve to a higher stage of the disease, i.e., these subjects are diagnosed with a high recurrence risk prostate cancer (also termed aggressive prostate cancer, biochemically recurrent prostate cancer or relapsing prostate cancer).

In one embodiment, a "high recurrence risk" means that a subject is expected to have distant metastases of prostate cancer within 2, preferably 3, 5, 8 or 10 years. In one embodiment, a high recurrence risk means that a subject is expected to have biochemical recurrence of prostate cancer within 2, preferably 3, 5, 8 or 10 years. In one embodiment, a high recurrence risk means that a subject is expected to have relapse of prostate cancer within 2, preferably 3, 5, 8 or 10 years.

In one embodiment, the subject is assigned to a low recurrence risk group, i.e., is diagnosed with an indolent prostate cancer, if:
  at least 1 prostate cancer marker selected from COMP is underexpressed, and
  at least 1 prostate cancer marker selected from CD38 is overexpressed,
with respect to the reference signature.

In one embodiment, the subject is assigned to a low recurrence risk group, i.e., is diagnosed with an indolent prostate cancer, if:
  at least 1, 2, preferably the 3 prostate cancer markers selected from COMP, KHDRBS3 and SFRP4 is/are underexpressed, and
  at least 1, 2, preferably the 3 prostate cancer markers selected from ANPEP, AZGP1 and CHRNA2 is/are overexpressed,
with respect to the reference signature.

In one embodiment, the subject is assigned to a low recurrence risk group, i.e., is diagnosed with an indolent prostate cancer, if:
  at least 1, 2, 3, 4, preferably the 5 prostate cancer markers selected from ASPN, COL10A1, COMP, CXCL14 and SFRP4 is/are underexpressed, and
  at least 1, preferably the 2 prostate cancer markers selected from CD38 and NCAPD3 is/are overexpressed, with respect to the reference signature.

In one embodiment, the subject is assigned to a low recurrence risk group, i.e., is diagnosed with an indolent prostate cancer, if:
  at least 1, 2, 3, 4, preferably the 5 prostate cancer markers selected from ANTXR1, COMP, KHDRBS3, MS4A6A and SFRP4 is/are underexpressed, and
  at least 1, 2, preferably the 3 prostate cancer markers selected from ANPEP, AZGP1 and CHRNA2 is/are overexpressed,
with respect to the reference signature.

In one embodiment, the subject is assigned to a low recurrence risk group, i.e., is diagnosed with an indolent prostate cancer, if:
  at least 1, 2, 3, 4, preferably the 5 prostate cancer markers selected from COL1A1, COMP, KHDRBS3, SFRP4 and VCAN is/are underexpressed, and
  at least 1, 2, 3, 4, 5, 6, 7, 8, 9, preferably the 10 prostate cancer markers selected from ACADL, ANPEP, AZGP1, CHRNA2, FMOD, GPT2, NCAPD3, REPS2, SLC15A2 and SLC22A3 is/are overexpressed,
with respect to the reference signature.

In one embodiment, the subject is assigned to a low recurrence risk group, i.e., is diagnosed with an indolent prostate cancer, if:
  at least 1, 2, 3, 4, 5, 6, 7, preferably the 8 prostate cancer markers selected from ASPN, COL10A1, COMP, CXCL14, KHDRBS3, SFRP2, SFRP4 and VCAN is/are underexpressed, and
  at least 1, 2, 3, 4, 5, 6, 7, preferably the 8 prostate cancer markers selected from AFF3, AZGP1, CD38, CHRNA2, FMOD, NCAPD3, SLC15A2 and SLC22A3 is/are overexpressed,
with respect to the reference signature.

In one embodiment, the subject is assigned to a low recurrence risk group, i.e., is diagnosed with an indolent prostate cancer, if:
  at least 1, 2, 3, 4, 5, preferably the 6 prostate cancer markers selected from ANTXR1, COL1A2, COL3A1, FRZB, KHDRBS3 and MS4A6A is/are underexpressed, and
  at least 1, 2, 3, 4, 5, 6, 7, 8, 9, preferably the 10 prostate cancer markers selected from AFF3, CHRNA2, FAM3B, FMOD, GPT2, HGD, NCAPD3, SLC15A2, SLC22A3 and STXBP6 is/are overexpressed, with respect to the reference signature.

In one embodiment, the subject is assigned to a low recurrence risk group, i.e., is diagnosed with an indolent prostate cancer, if:
  at least 1, 2, 3, 4, 5, 6, 7, preferably the 8 prostate cancer markers selected from ANTXR1, COL1A1, COL3A1, COMP, ITGBL1, KHDRBS3, SFRP4 and SPARC is/are underexpressed, and
  at least 1, 2, 3, 4, 5, 6, 7, 8, 9, preferably the 10 prostate cancer markers selected from ACADL, ANPEP, AZGP1, CHRNA2, FMOD, GPT2, NCAPD3, REPS2, SLC15A2 and SLC22A3 is/are overexpressed,
with respect to the reference signature.

In one embodiment, the subject is assigned to a low recurrence risk group, i.e., is diagnosed with an indolent prostate cancer, if:
  at least 1, 2, 3, 4, 5, 6, 7, 8, 9, 10, 11, 12, 13, 14, 15, 16, 17, preferably the 18 prostate cancer markers selected from ASPN, COL1A1, COL1A2, COL3A1, COL8A1, COL10A1, COMP, CPXM2, CXCL14, FRZB, KHDRBS3, MGP, NOX4, SFRP2, SFRP4, SULF1, THBS2 and VCAN is/are underexpressed, and
  at least 1, 2, 3, 4, 5, 6, 7, 8, 9, 10, 11, 12, 13, 14, preferably the 15 prostate cancer markers selected from ACADL, AFF3, ANO7, ANPEP, AZGP1, CD38, CHRNA2, FAM3B, FMOD, GPT2, HGD, NCAPD3, REPS2, SLC15A2 and SLC22A3 is/are overexpressed,
with respect to the reference signature.

In one embodiment, the subject is assigned to a low recurrence risk group, i.e., is diagnosed with an indolent prostate cancer, if:
  at least 1, 2, 3, 4, 5, 6, 7, 8, 9, 10, 11, 12, 13, 14, 15, 16, 17, 18, 19, 20, 21, 22, preferably the 23 prostate cancer markers selected from ANTXR1, ASPN, CDH11, COL1A, COL1A2, COL3A, COL8A, COL10A1, COMP, CPXM2, CXCL14, FRZB, ITGBL1, KHDRBS3, MGP, MS4A6A, NOX4, SFRP2, SFRP4, SPARC, SULF1, THBS2 and VCAN is/are underexpressed, and at least 1, 2, 3, 4, 5, 6, 7, 8, 9, 10, 11, 12, 13, 14, 15, preferably the 16 prostate cancer markers selected from ACADL, AFF3, ANO7, ANPEP, AZGP1, CD38, CHRNA2, FAM3B, FMOD, GPT2, HGD, NCAPD3, REPS2, SLC15A2, SLC22A3 and STXBP6 is/are overexpressed, with respect to the reference signature.

In one embodiment, the reference signature is derived from a reference population comprising subjects diagnosed with indolent prostate cancer. In one embodiment, the reference signature is derived from a reference population comprising subjects diagnosed with aggressive prostate cancer.

In one embodiment, the subject is assigned to a low recurrence risk, a high recurrence risk or an undefined group, if the molecular signature of the sample from said subject has the highest correlation with the low risk, high risk or undefined centroid, respectively.

In one embodiment, the subject is assigned to a low recurrence risk, a high recurrence risk or an undefined group, if the group whose centroid is closest to the molecular signature, in Pearson correlation distance, is predicted to be the group for the sample.

In one embodiment, the molecular signature or the methods of the invention may be for classifying a subject as a biochemical recurrence-free survival subject, wherein biochemical recurrence-free survival means that the prostate cancer does not evolve, e.g., does not induce distant metastases within 2, preferably 3, 5, 8 or 10 years.

In one embodiment, the signature or the methods of the invention may be for assessing the likelihood of distal recurrence of the prostate cancer. In one embodiment, the term "distal recurrence" refers to recurrence within 2 years, preferably within 3, 5, 8 years, more preferably within 10 years. In one embodiment, the term "recurrence" may refer to the reappearance of cancer either within the prostate or elsewhere in the body.

In one embodiment, the signature or the methods of the invention may be for predicting overall survival of the subject, wherein the overall survival refers to the survival at 2 years, preferably at 3, 5, 8 years, more preferably at 10 years.

In one embodiment, the methods of the invention comprise the steps of:
a) providing a sample from the subject,
b) determining the TMPRSS/ERG fusion status of said sample,
c) if said sample is positive for TMPRSS/ERG fusion (Fus$^+$), determining the molecular signature according to the invention of said sample,
d) comparing the molecular signature with a reference signature obtained from a reference population, and
e) assigning the subject to a risk group based on the correlation of the molecular signature with the reference signature, thereby predicting the risk of prostate cancer recurrence in said subject.

In one embodiment, the expression of at least 1, preferably of at least 2 prostate cancer markers is assessed. In one embodiment, the methods of the invention comprise the steps of:
a) providing a sample from the subject,
b) determining the TMPRSS/ERG fusion status of said sample,
c) if said sample is positive for TMPRSS/ERG fusion (Fus$^+$), determining the molecular signature according to the invention of said sample by measuring the expression level of at least one prostate cancer marker, preferably of at least 2 prostate cancer markers selected from the group comprising or consisting of CD38 and COMP,
d) comparing the molecular signature to a reference signature obtained from a reference population, and
e) assigning the subject to a risk group based on the correlation of the molecular signature with the reference signature, thereby predicting the risk of prostate cancer recurrence in said subject.

In one embodiment, the expression of at least 1, preferably at least 2, 3, 4, 5, more preferably of 6 prostate cancer markers is assessed. In one embodiment, the methods of the invention comprise the steps of:
a) providing a sample from the subject,
b) determining the TMPRSS/ERG fusion status of said sample,
c) if said sample is positive for TMPRSS/ERG fusion (Fus$^+$), determining the molecular signature according to the invention of said sample by measuring the expression level of at least one prostate cancer marker, preferably at least 2, 3, 4, 5, more preferably of 6 prostate cancer markers selected from the group comprising or consisting of ANPEP, AZGP1, CHRNA2, COMP, KHDRBS3 and SFRP4,
d) comparing the molecular signature to a reference signature obtained from a reference population, and
e) assigning the subject to a risk group based on the correlation of the molecular signature with the reference signature, thereby predicting the risk of prostate cancer recurrence in said subject.

In one embodiment, the expression of at least 1, preferably at least 2, 3, 4, 5, 6, more preferably of 7 prostate cancer markers is assessed. In one embodiment, the methods of the invention comprise the steps of:
a) providing a sample from the subject,
b) determining the TMPRSS/ERG fusion status of said sample,
c) if said sample is positive for TMPRSS/ERG fusion (Fus$^+$), determining the molecular signature according to the invention of said sample by measuring the expression level of at least one prostate cancer marker, preferably at least 2, 3, 4, 5, 6, more preferably of 7 prostate cancer markers selected from the group comprising or consisting of ASPN, CD38, COL10A1, COMP, CXCL14, NCAPD3 and SFRP4,
d) comparing the molecular signature to a reference signature obtained from a reference population, and
e) assigning the subject to a risk group based on the correlation of the molecular signature with the reference signature, thereby predicting the risk of prostate cancer recurrence in said subject.

In one embodiment, the expression of at least 1, preferably at least 2, 3, 4, 5, 6, 7, more preferably of 8 prostate cancer markers is assessed. In one embodiment, the methods of the invention comprise the steps of:
a) providing a sample from the subject,
b) determining the TMPRSS/ERG fusion status of said sample,
c) if said sample is positive for TMPRSS/ERG fusion (Fus$^+$), determining the molecular signature according to the invention of said sample by measuring the expression level of at least one prostate cancer marker, preferably at least 2, 3, 4, 5, 6, 7, more preferably of 8 prostate cancer markers selected from the group comprising or consisting of ANPEP, ANTXR1, AZGP1, CHRNA2, COMP, KHDRBS3, MS4A6A and SFRP4, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably at least 2, 3, 4, 5, 6, 7, 8, 9, 10, 11, 12, 13, 14, more preferably of 15 prostate cancer markers is assessed. In one embodiment, the methods of the invention comprise the steps of:

a) providing a sample from the subject, b) determining the TMPRSS/ERG fusion status of said sample, c) if said sample is positive for TMPRSS/ERG fusion (Fus$^+$), determining the molecular signature according to the invention of said sample by measuring the expression level of at least one prostate cancer marker, preferably at least 2, 3, 4, 5, 6, 7, 8, 9, 10, 11, 12, 13, 14, more preferably of 15 prostate cancer markers selected from the group comprising or consisting of ACADL, ANPEP, AZGP1, CHRNA2, COL1A1, COMP, FMOD, GPT2, KHDRBS3, NCAPD3, REPS2, SFRP4, SLC15A2, SLC22A3 and VCAN, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably of at least 2, 3, 4, 5, 6, 7, 8, 9, 10, 11, 12, 13, 14, 15, more preferably of 16 prostate cancer markers is assessed. In one embodiment, the methods of the invention comprise the steps of:

a) providing a sample from the subject, b) determining the TMPRSS/ERG fusion status of said sample, c) if said sample is positive for TMPRSS/ERG fusion (Fus$^+$), determining the molecular signature according to the invention of said sample by measuring the expression level of at least one prostate cancer marker, preferably at least 2, 3, 4, 5, 6, 7, 8, 9, 10, 11, 12, 13, 14, 15, more preferably of 16 prostate cancer markers selected from the group comprising or consisting of AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably of at least 2, 3, 4, 5, 6, 7, 8, 9, 10, 11, 12, 13, 14, 15, more preferably of 16 prostate cancer markers is assessed. In one embodiment, the methods of the invention comprise the steps of:

a) providing a sample from the subject, b) determining the TMPRSS/ERG fusion status of said sample, c) if said sample is positive for TMPRSS/ERG fusion (Fus$^+$), determining the molecular signature according to the invention of said sample by measuring the expression level of at least one prostate cancer marker, preferably of at least 2, 3, 4, 5, 6, 7, 8, 9, 10, 11, 12, 13, 14, 15, more preferably of 16 prostate cancer markers selected from the group comprising or consisting of AFF3, ANTXR1, CHRNA2, COL1A2, COL3A1, FAM3B, FMOD, FRZB, GPT2, HGD, KHDRBS3, MS4A6A, NCAPD3, SLC15A2, SLC22A3 and STXBP6, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably of at least 2, 3, 4, 5, 6, 7, 8, 9, 10, 11, 12, 13, 14, 15, 16, 17, more preferably of 18 prostate cancer markers is assessed. In one embodiment, the methods of the invention comprise the steps of:

a) providing a sample from the subject, b) determining the TMPRSS/ERG fusion status of said sample, c) if said sample is positive for TMPRSS/ERG fusion (Fus$^+$), determining the molecular signature according to the invention of said sample by measuring the expression level of at least one prostate cancer marker, preferably of at least 2, 3, 4, 5, 6, 7, 8, 9, 10, 11, 12, 13, 14, 15, 16, 17, more preferably of 18 prostate cancer markers selected from the group comprising or consisting of ACADL, ANPEP, ANTXR1, AZGP1, CHRNA2, COL1A1, COL3A, COMP, FMOD, GPT2, ITGBL1, KHDRBS3, NCAPD3, REPS2, SFRP4, SLC15A2, SLC22A3 and SPARC, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, more preferably of 33 prostate cancer markers is assessed. In one embodiment, the methods of the invention comprise the steps of:

a) providing a sample from the subject, b) determining the TMPRSS/ERG fusion status of said sample, c) if said sample is positive for TMPRSS/ERG fusion (Fus$^+$), determining the molecular signature according to the invention of said sample by measuring the expression level of at least one prostate cancer marker, preferably of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, more preferably of 33 prostate cancer markers selected from the group comprising or consisting of ACADL, AFF3, ANO7, ANPEP, ASPN, AZGP1, CD38, CHRNA2, COL1A1, COL1A2, COL3A, COL8A, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN, d) comparing the molecular signature to a reference signature obtained from a reference population, and e) assigning the subject to a risk group based on the correlation of the molecular signature with the reference signature, thereby predicting the risk of prostate cancer recurrence in said subject.

In one embodiment, the expression of at least 1, preferably of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, more preferably of 39 prostate cancer markers is assessed. In one embodiment, the methods of the invention comprise the steps of:
  a) providing a sample from the subject,
  b) determining the TMPRSS/ERG fusion status of said sample,
  c) if said sample is positive for TMPRSS/ERG fusion (Fus$^+$), determining the molecular signature according to the invention of said sample by measuring the expression level of at least one prostate cancer marker, preferably of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, more preferably of 39 prostate cancer markers selected from the group comprising or consisting of ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN,
  d) comparing the molecular signature to a reference signature obtained from a reference population, and
  e) assigning the subject to a risk group based on the correlation of the molecular signature with the reference signature, thereby predicting the risk of prostate cancer recurrence in said subject.

In one embodiment, the subject is a man.

In one embodiment, the subject is a child. In one embodiment, the subject is an adult.

In one embodiment, the subject is above 40 years old. In one embodiment, the subject is above 50 years old. In one embodiment, the subject is above 60 years old. In one embodiment, the subject is above 70 years old. In one embodiment, the subject is above 80 years old.

In one embodiment, the subject is aged from 0 to 20 years old. In one embodiment, the subject is aged from 20 to 40 years old. In one embodiment, the subject is aged from 40 to 50 years old. In one embodiment, the subject is aged from 50 to 55 years old. In one embodiment, the subject is aged from 55 to 60 years old. In one embodiment, the subject is aged from 60 to 65 years old. In one embodiment, the subject is aged from 65 to 70 years old. In one embodiment, the subject is aged from 70 to 75 years old. In one embodiment, the subject is aged from 75 to 80 years old. In one embodiment, the subject is aged from 80 to 85 years old. In one embodiment, the subject is aged from 85 to 90 years old.

In one embodiment, the subject is diagnosed with prostate cancer. In another embodiment, the subject is at risk of prostate cancer. Examples of risks include, but are not limited to, familial history of prostate cancer, genetic predisposition to prostate cancer, environmental risks such as, for example, exposure to carcinogenic chemicals or other types of carcinogenic agents, diet, clinical factors such as, for example, hormonal deregulation or presence of another cancer-inducing disease, and the like.

In one embodiment, the subject is a prostate cancer patient. In one embodiment, the subject is a patient with prostatic adenocarcinoma. In one embodiment, the subject is a patient with prostatic sarcoma.

In one embodiment, the subject previously received an anticancer treatment. In one embodiment, the subject did not receive any anticancer treatment. Examples of anticancer treatment include, but are not limited to, surgery for removing the tumor, surgery for removing the whole affected organ (in the present invention, surgery for removing the whole prostate is termed "prostatectomy"), chemotherapy and/or radiotherapy.

In one embodiment, the subject was previously treated for a prostate cancer. In one embodiment, the subject is considered as substantially healthy as regard to this prostate cancer, i.e., the treatment is considered to have been successful.

In one embodiment, the subject was previously diagnosed as Fus+, i.e., the subject has a positive TMPRSS/ERG fusion status, indicating that the TMPRSS/ERG fusion is present in a sample from said subject.

In one embodiment, the subject was previously diagnosed as Fus$^-$, i.e., the subject has a negative TMPRSS/ERG fusion status, indicating that the TMPRSS/ERG fusion is absent in a sample from said subject.

Experts skilled in the art will recognize that there are numerous ways to diagnose the TMPRSS/ERG fusion status in a subject, including, but not limited to, RT-PCR, qPCR, high-throughput sequencing (Mertz et al., 2007. *Neoplasia*. 9(3):200-206; Maher et al., 2009. *Nature*. 458(7234):97-101), immunohistochemistry tests (Chaux et al., 2011. *Am J Surg Pathol*. 35(7):1014-20) and urine-based test (Koo et al., 2016. *Sci Rep*. 6:30722).

In one embodiment, the signature of the present invention further comprises the TMPRSS/ERG fusion marker. In one embodiment, the methods of the present invention further comprise a step of determining the TMPRSS/ERG fusion status of the subject.

The present invention also relates to a method for treating a subject affected with indolent prostate cancer, comprising the steps of:
  a) providing a sample from the subject,
  b) determining the TMPRSS/ERG fusion status in said sample,
  c) if said sample is positive for TMPRSS/ERG fusion (Fus$^+$), determining the molecular signature according to the invention of said sample,
  d) comparing the molecular signature with a reference signature obtained from a reference population,
  e) assigning the subject to a risk group based on the correlation of the molecular signature with the reference signature, thereby predicting the risk of prostate cancer recurrence in said subject, and
  f) placing said subject under active surveillance if the subject was assigned to a low risk group in step e).

The present invention also relates to a kit for measuring the expression level of at least one prostate cancer marker, for determining the molecular signature of a sample according to the present invention and/or for implementing the methods of the invention.

In one embodiment, the kit comprises or consists of means for determining the expression levels of at least one prostate cancer marker according to the invention.

In one embodiment, the expression profile is measured at the protein level, and the kit of the invention comprises or consists of means for total protein extraction, as well as antibodies for detecting at least one prostate cancer marker according to the invention.

In another embodiment, the expression profile is measured at the RNA level, and the kit of the invention comprises or consists of means for total RNA extraction, means for reverse transcription of total RNA, and means for quantifying the expression level of RNA corresponding to at least one prostate cancer marker according to the invention.

In one embodiment, the means for determining the expression level of at least one prostate cancer marker according to the invention are PCR primers, preferably qPCR primers, specific for said prostate cancer markers. In one embodiment, said means for determining the expression levels of at least one prostate cancer marker comprises probes to detect qPCR amplicons obtained with qPCR primers as hereinabove described.

In one embodiment, said means for quantifying the expression levels of RNA corresponding to the prostate cancer markers according to the invention is PCR, preferably qPCR.

In one embodiment, the kit of the invention may also comprise primers for amplifying reference genes. Reference genes are genes expressed at a constant level among different tissues and/or conditions. Examples of reference genes include, but are not limited to, β-actin, genes encoding ribosomal proteins and the like.

In one embodiment, the kit of the invention may also comprise means for total RNA extraction, means for reverse transcription of total RNA, and reagents for carrying out a quantitative PCR as hereinabove described (such as, for example, primers, buffers, enzyme, and the like). In one embodiment, the kit of the invention may also comprise a reference sample.

In one embodiment of the invention, the kit of the invention comprises DNA probes, which may be hybridized to the qPCR amplicons to detect at least one prostate cancer marker according to the invention.

In one embodiment, the means for determining the expression levels of the prostate cancer markers according to the present invention is a microarray comprising or consisting of probes specific for at least one prostate cancer marker as described hereinabove.

In one embodiment, said means for quantifying the expression level of RNA corresponding to the prostate cancer markers of the invention is a microarray. The present invention thus also relates to microarrays for measuring the RNA expression profile of at least one prostate cancer marker of the invention, for determining the molecular signature according to the present invention and/or for implementing the methods of the invention.

In one embodiment, the microarray of the invention comprises or consists of DNA probes, which may be hybridized to the retro-transcribed RNA corresponding to at least one prostate cancer marker according to the invention.

In one embodiment of the invention, the microarray of the invention comprises or consists of probes specific of at least one prostate cancer marker according to the invention.

In one embodiment of the invention, the microarray of the invention comprises or consists of probes specific of at least one prostate cancer marker, preferably at least 2 prostate cancer markers selected from CD38 and COMP.

In one embodiment of the invention, the microarray of the invention comprises or consists of probes specific of at least one prostate cancer marker, preferably at least 2, 3, 4, 5, more preferably of 6 prostate cancer markers selected from ANPEP, AZGP1, CHRNA2, COMP, KHDRBS3 and SFRP4.

In one embodiment of the invention, the microarray of the invention comprises or consists of probes specific of at least one prostate cancer marker, preferably at least 2, 3, 4, 5, 6, more preferably of 7 prostate cancer markers selected from ASPN, CD38, COL10A1, COMP, CXCL14, NCAPD3 and SFRP4.

In one embodiment of the invention, the microarray of the invention comprises or consists of probes specific of at least one prostate cancer marker, preferably at least 2, 3, 4, 5, 6, 7, more preferably of 8 prostate cancer markers selected from ANPEP, ANTXR1, AZGP1, CHRNA2, COMP, KHDRBS3, MS4A6A and SFRP4.

In one embodiment of the invention, the microarray of the invention comprises or consists of probes specific of at least one prostate cancer marker, preferably at least 2, 3, 4, 5, 6, 7, 8, 9, 10, 11, 12, 13, 14, more preferably of 15 prostate cancer markers selected from ACADL, ANPEP, AZGP1, CHRNA2, COL1A1, COMP, FMOD, GPT2, KHDRBS3, NCAPD3, REPS2, SFRP4, SLC15A2, SLC22A3 and VCAN.

In one embodiment of the invention, the microarray of the invention comprises or consists of probes specific of at least one prostate cancer marker, preferably at least 2, 3, 4, 5, 6, 7, 8, 9, 10, 11, 12, 13, 14, 15, more preferably of 16 prostate cancer markers selected from AFF3, ASPN, AZGP1, CD38, CHRNA2, COL10A1, COMP, CXCL14, FMOD, KHDRBS3, NCAPD3, SFRP2, SFRP4, SLC15A2, SLC22A3 and VCAN.

In one embodiment of the invention, the microarray of the invention comprises or consists of probes specific of at least one prostate cancer marker, preferably at least 2, 3, 4, 5, 6, 7, 8, 9, 10, 11, 12, 13, 14, 15, more preferably of 16 prostate cancer markers selected from AFF3, ANTXR1, CHRNA2, COL1A2, COL3A, FAM3B, FMOD, FRZB, GPT2, HGD, KHDRBS3, MS4A6A, NCAPD3, SLC15A2, SLC22A3 and STXBP6.

In one embodiment of the invention, the microarray of the invention comprises or consists of probes specific of at least one prostate cancer marker, preferably at least 2, 3, 4, 5, 6, 7, 8, 9, 10, 11, 12, 13, 14, 15, 16, 17, more preferably of 18 prostate cancer markers selected from ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC.

In one embodiment of the invention, the microarray of the invention comprises or consists of probes specific of at least one prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, more preferably of 33 prostate cancer markers selected from ACADL, AFF3, ANO7, ANPEP, ASPN, AZGP1, CD38, CHRNA2, COL1A1, COL1A2, COL3A1, COL8A1, COL10A1, COMP, CPXM2, CXCL14, FAM3B, FMOD, FRZB, GPT2, HGD, KHDRBS3, MGP, NCAPD3, NOX4, REPS2, SFRP2, SFRP4, SLC15A2, SLC22A3, SULF1, THBS2 and VCAN.

In one embodiment of the invention, the microarray of the invention comprises or consists of probes specific of at least one prostate cancer marker, preferably at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, more preferably of 39 prostate cancer markers selected from ACADL, AFF3, ANO7, ANPEP, ANTXR1, ASPN, AZGP1, CD38, CDH11, CHRNA2, COL10A1, COL1A1, COL1A2, COL3A, COL8A, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN.

In one embodiment, probes specific of at least one prostate cancer marker according to the invention are commercially available and can be readily purchased by the one skilled in the art.

Examples of probes specific of at least one prostate cancer marker include probes from the Human Gene 2.1 ST Array (Affymetrix). In one embodiment, probes from the Human Gene 2.1 ST Array (Affymetrix), specific of at least one prostate cancer marker according to the present invention, are listed in Table 1.

Further examples of probes specific of at least one prostate cancer marker include probes from the Human Exon 1.0 ST Array (Affymetrix). In one embodiment, probes from the Human Exon 1.0 ST Array (Affymetrix), specific of at least one prostate cancer marker according to the present invention, are listed in Table 1.

Further examples of probes specific of at least one prostate cancer marker include probes from the HTA-2_0 Array (Affymetrix). In one embodiment, probes from the HTA-2_0 Array (Affymetrix), specific of at least one prostate cancer marker according to the present invention, are listed in Table 1.

TABLE 1 transcript cluster IDs of probes specific of the prostate cancer markers according to the present invention, from the Human genes 2.1 ST Array (Affymetrix), Human Exon 1.0 ST Array (Affymetrix) and HTA-2_0 Array (Affymetrix). Probes sequences are available on NetAffx ™ Analysis Center at affymetrix.com

| Gene name | Human genes 2.1 ST Array (Affymetrix) | Human Exon 1.0 ST Array (Affymetrix) | HTA-2_0 Array (Affymetrix) |
|---|---|---|---|
| COMP | 16870453 | 3855218 | TC19001293.hg.1 |
| COL10A1 | 17022929 | 2922581 | TC06002044.hg.1 |
| GPT2 | 16818610 | 3690073 | TC16000426.hg.1 |
| ITGBL1 | 16776160 | 3523483 | TC13000364.hg.1 |
| NOX4 | 16743148 | 3330301 | TC11002178.hg.1 |
| SFRP4 | 17056791 | 3046444 | TC07001293.hg.1 |
| KHDRBS3 | 17072979 | 3155015 | TC08000778.hg.1 |
| NCAPD3 | 16746379 | 3399545 | TC11002473.hg.1 |
| ASPN | 17095887 | 3179423 | TC09001336.hg.1 |
| REPS2 | 17101828 | 3970307 | TCOX000082.hg.1 |
| VCAN | 16986913 | 2865300 | TC05000412.hg.1 |
| COL1A1 | 16846587 | 3762198 | TC17001682.hg.1 |
| ANTXR1 | 16881031 | 2487246 | TC02000403.hg.1 |
| THBS2 | 17025844 | 2985781 | TC06002330.hg.1 |
| CDH11 | 16827041 | 3664285 | TC16001165.hg.1 |
| HGD | 16957906 | 2638456 | TC03001692.hg.1 |
| CHRNA2 | 17075712 | 3129024 | TC08001080.hg.1 |
| SPARC | 17001927 | 2835937 | TC05001955.hg.1 |
| AZGP1 | 17060380 | 3015100 | TC07001652.hg.1 |
| SLC15A2 | 16944588 | 2638728 | TC03000625.hg.1 |
| CXCL14 | 17000168 | 2876608 | TC05001804.hg.1 |
| STXBP6 | 16791455 | 3558520 | TC14000983.hg.1 |
| ANO7 | 16893414 | 2536217 | TC02001476.hg.1 |
| CPXM2 | 16719171 | 4038377 | TC10001721.hg.1 |
| MS4A6A | 16738819 | 3332294 | TC11001839.hg.1 |
| ACADL | 16907812 | 2597347 | TC02002731.hg.1 |
| SFRP2 | 16980762 | 2790368 | TC04001651.hg.1 |
| SULF1 | 17069816 | 3102472 | TC08000456.hg.1 |
| SLC22A3 | 17014442 | 2934521 | TC06001156.hg.1 |
| CD38 | 16965268 | 2719706 | TC04000145.hg.1 |
| FRZB | 16906175 | 2518677 | TC02002591.hg.1 |
| COL8A1 | 16943241 | 2686201 | TC03000502.hg.1 |
| COL3A1 | 16888610 | 2591634 | TC02001105.hg.1 |
| MGP | 16761820 | 3445741 | TC12001276.hg.1 |
| FAM3B | 16922943 | 3933002 | TC21000187.hg.1 |
| FMOD | 16698234 | 2375680 | TC01003722.hg.1 |
| COL1A2 | 17048473 | 3061757 | TC07000559.hg.1 |
| AFF3 | 16901068 | 2567083 | TC02002136.hg.1 |
| ANPEP | 16813206 | 3638607 | TC15001837.hg.1 |

Further examples of probes specific of at least one prostate cancer marker include probes from the HumanHT-12 v4 Array (Illumina). In one embodiment, probes from the HumanHT-12 v4 Array (Illumina), specific of at least one prostate cancer marker according to the present invention, are listed in Table 2.

TABLE 2

Probe IDs, sequences and SEQ ID NOs of probes specific of the prostate cancer markers according to the present invention, from the HumanHT-12 v4 Array (Illumina). Probes sequences are available at illumina.com

| SEQ ID NO | Gene name | Illumina Probe ID | Sequence |
|---|---|---|---|
| 1 | COMP | ILMN_1677636 | AGAGGACTATGAGACCCATCAGCTGCGGCAAGCCTAGGGACCAGGGTGAG |
| 2 | COL10A1 | ILMN_1672776 | CCCCTAAAATATTTCTGATGGTGCACTACTCTGAGGCCTGTATGGCCCCT |
| 3 | GPT2 | ILMN_1684158 | CCTGTGGCTGTTTTCCCGTCTAGGTTCTCACAGGTATCTCCTGACAGAGG |
| 4 | ITGBL1 | ILMN_1653719 | GGGGACAATGAAGACAAGCACACAGGAGGTAGAATATCAGAGTGGGGCTG |
| 5 | NOX4 | ILMN_1735996 | TGAGGAGCTGAACTTGCTCAATCTAAGGCTGATTGTCGTGTTCCTCTTTA |
| 6 | SFRP4 | ILMN_1810172 | GTTCAGGACAAGAAGAAAACAGCCGGGCGCACCAGTCGTAGTAATCCCCC |
| 7 | KHDRBS3 | ILMN_1691747 | AGGCACCTTCAGCGAGGACAGCAAAGGGCGTCTACAGAGACCAGCCATAT |
| 8 | NCAPD3 | ILMN_1683441 | TGTGGAACACGAGAGCTCCTCCTCAGGGGCCTGGCACTCACCTTCTATTC |
| 9 | ASPN | ILMN_1875691 | CGTGTATGTGACTCAGTTTCCATGGCTTAACTGTTTCTGCTGGCATAACC |
| 10 | REPS2 | ILMN_1656934 | CCCCCCATGGTTCAAGTGACAGTGGGTGACCTTGTCTGCCAAGATCTTTC |
| 11 | VCAN | ILMN_1687301 | CAGCCATAGGTGCAGTTTGCTTCTACATGATGCTAAAGGCTGCGAATGGG |
| 12 | COL1A1 | ILMN_1701308 | TCCCTCCTAGTCTGTCCTGCGTCCTCTGTCCCGGGTTTCAGAGACAACT |
| 13 | ANTXR1 | ILMN_1670379 | ACCATGCTATAGGAGACTGGGCAAAACCTGTACAATGACAACCCTGGAAG |
| 14 | THBS2 | ILMN_1678842 | GACTGTCAACAGCGTGCAGGTTTTCTGTTTCTGTGTTGTGGGGTCAACCG |
| 15 | CDH11 | ILMN_1672611 | CGTGCCAGATATAACTGTCTTGTTTCAGTGAGAGACGCCCTATTTCTATG |
| 16 | HGD | ILMN_2198239 | GGGAGCCACTCAAGAGCCACTTCACTCCCAACTCCAGGAACCCAGCAGAA |
| 17 | CHRNA2 | ILMN_1698849 | TCATTCCTCTCCTTCCTTGCTGCAAAATGGCTCTGCACCAGCCGGCCCCC |
| 18 | SPARC | ILMN_1796734 | CGCAGCTCCCCAATCACACTAGCAACATTTCAAGTGCTTGAGAGCCATGC |

TABLE 2-continued

Probe IDs, sequences and SEQ ID NOs of probes specific of the prostate cancer markers according to the present invention, from the HumanHT-12 v4 Array (Illumina). Probes sequences are available at illumina.com

| SEQ ID NO | Gene name | Illumina Probe ID | Sequence |
|---|---|---|---|
| 19 | AZGP1 | ILMN_1797154 | TGAGGAGCAGTGTGGGGGACAGACAGGAGGTGGATTTGGAGACCGAAGA |
| 20 | SLC15A2 | ILMN_2211739 | CTTGTGCAGTGTTGCTGGAGCTGGCCTGGTGTCTCCAAATGACCATGAAA |
| 21 | CXCL14 | ILMN_1748323 | CCTCTGTACATATACCCTTAAGAACGCCCCCTCCACACACTGCCCCCCAG |
| 22 | STXBP6 | ILMN_2172969 | GATTTTGCTCCTTGCATAGTAATCTTTTGCATGAACCATCACCAGCGTTC |
| 23 | ANO7 | ILMN_1683824 | GCTCACAAGGCCCTCTTTGTTTCCTGCTCCCAGACATAAGCCCAAGGGGC |
| 24 | CPXM2 | ILMN_1741688 | CCAGAAGTGGGGTGGCCTGAAGCCCTCTCTCTGCTTGAGGTATTGCCCCT |
| 25 | MS4A6A | ILMN_2359800 | GGGACTATCCAGATCTTGTGTGGCATGATGGTATTGAGCTTGGGGATCAT |
| 26 | ACADL | ILMN_1660890 | GAAGCTGGAAGCCATCATACCTTACTGCCTTGAAACCCCTAGGACTCAGC |
| 27 | SFRP2 | ILMN_1722898 | GGCCCAAACTTGTGGGTCACAAACCCTGTTGAGATAAAGCTGGCTGTTAT |
| 28 | SULF1 | ILMN_1702363 | CCTCACTGAGTCATCAGTACCCTCCTATTCAGCTCCCCAAGATGATGTGT |
| 29 | SLC22A3 | ILMN_2048478 | CTGAGATCTGGGTTTAACGATCTGGGCTTTGTCATGGTGTTTTACGTTCG |
| 30 | CD38 | ILMN_2233783 | TACATGACTCAGCATACCTGCTGGTGCAGAGCTGAAGATTTTGGAGGGTC |
| 31 | FRZB | ILMN_1716246 | GCCTGATTGAGAAGCACAACTGAAACCAGTAGCCGCTGGGGTGTTAATGG |
| 32 | COL8A1 | ILMN_1685433 | GAGACCGGGTGTTCCTCCAGATGCCCTCAGAACAGGCTGCAGGACTGTAT |
| 33 | COL3A1 | ILMN_1773079 | TCAACTGCTTGTAAAGGTGCTCCTCTTTTTTCTTGTCATTGCTGGTCAAG |
| 34 | MGP | ILMN_1651958 | GGAGCCTCTCTCCCTACTGCTGCTACACAAGACCCTGAGACTGACCTGCA |
| 35 | FAM3B | ILMN_2355486 | CTGGACCGATGACAAAGTTTATTCAGAGTGCTGCTCCAAAATCCCTGCTC |
| 36 | FMOD | ILMN_1789639 | GGGGCAAGGACTGTTGGAGGAGAGTTAGCCCAAGTATAGGCTCTGCCCAG |
| 37 | COL1A2 | ILMN_2104356 | GATCCACATTGTTAGGTGCTGACCTAGACAGAGATGAACTGAGGTCCTTG |
| 38 | AFF3 | ILMN_1775235 | GTAGATTCCCAAGAGACTTTAGCAGTCACCAGCCTTAATGCATGTACAGG |
| 39 | ANPEP | ILMN_1763837 | CTCCAGCCCACGTTCTCTCTGCCTGTGAGCCAGTCTAGTTCCTGATGACC |

In one embodiment, probes specific of at least one prostate cancer marker according to the invention are selected from the group comprising or consisting of probes of Table 1 and/or of Table 2.

In one embodiment, the microarray of the invention may also comprise probes for quality control genes. Quality control genes expression allows verifying the quality of the microarray and/or of the cDNA applied on the microarray.

In one embodiment of the invention, the kit of the invention may also comprise means for total RNA extraction, means for reverse transcription of total RNA, and a microarray of the invention as well as buffers and materials for use thereof. In one embodiment, the kit of the invention also comprises a reference sample.

In one embodiment, the means for determining the expression level of prostate cancer markers according to the invention are sequencing means, allowing sequencing total RNA, preferably mRNA, or total cDNA of the sample from the subject, preferably using high-throughput sequencing technologies, more preferably using the RNA-Seq technology.

Examples of means for total sequencing of cDNA of a sample include, but are not limited to, poly(T) oligos, poly(T) magnetic beads, probes for removing ribosomal RNA, reverse transcriptase, emulsion PCR buffers and reagents, bridge amplification buffers and reagents, ligase and the like.

In one embodiment, the means for determining the expression levels of the prostate cancer markers according to the present invention is a CodeSet for said prostate cancer markers. Custom CodeSets for a given panel of markers are commercially available. These include, without limitation, nCounter® Custom CodeSets (NanoString).

Figure 1:
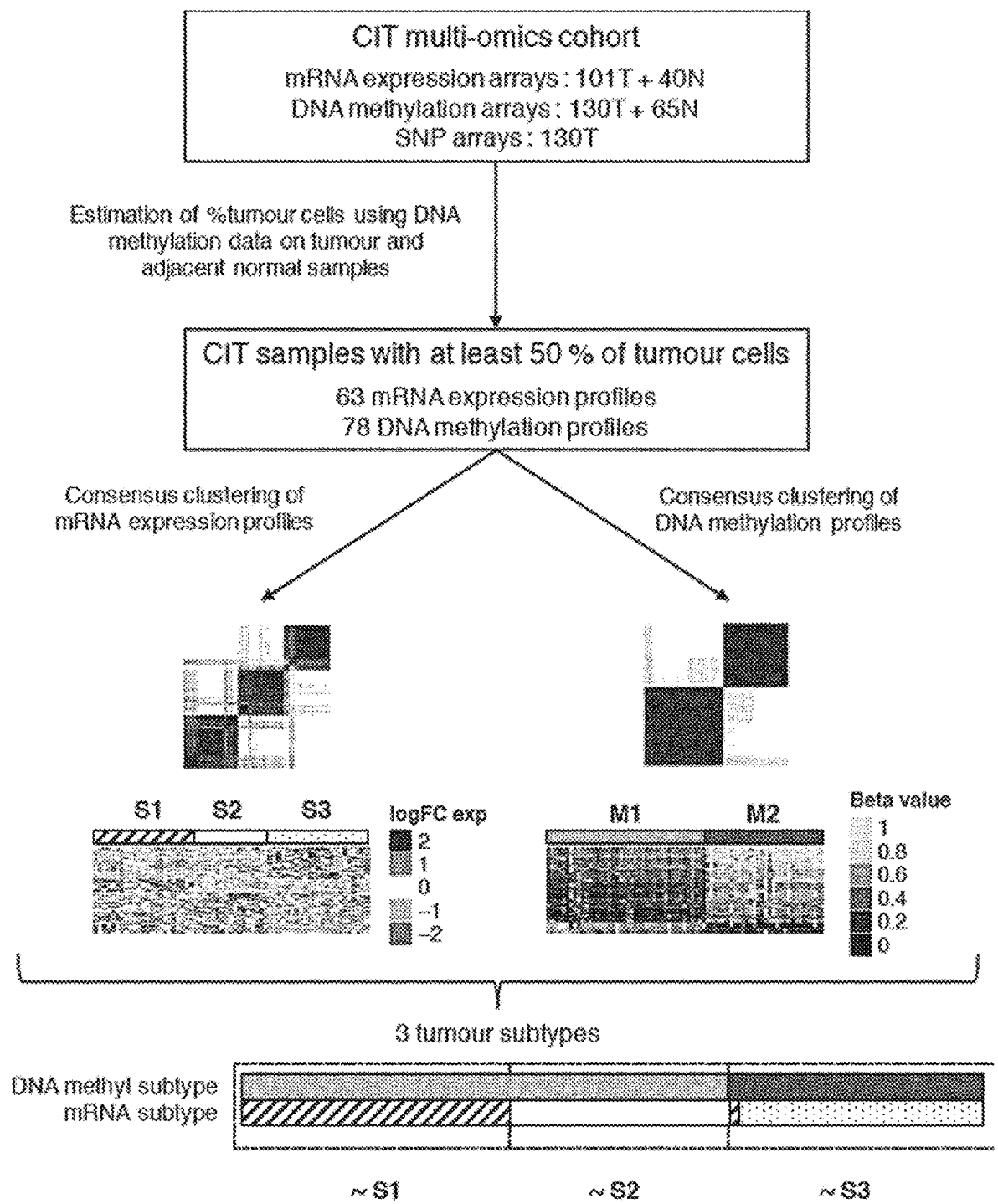
FIG. 1 is an illustration of the workflow used to analyze samples in the CIT cohort and hence identify 3 mRNA subtype (S1, S2 and S3) and 2 methylation subtypes. A multi-omics cohort of 195 samples (130 samples of localized prostate adenocarcinoma and 65 samples of adjacent normal samples) was analyzed to build a molecular classification of prostate cancer. We first used the series of DNA methylation arrays from tumor and normal samples in order to assess the percentage of tumor cells in each sample. Only tumor samples containing more that 50% of tumor cells were used to build a consensus classification of molecular data. Consensus clustering was performed separately on mRNA data and DNA methylation data and the resulting classes of each molecular layer were combined into three molecular subtypes summarizing almost perfectly the transcriptomic layer.

The prognostic significance of S2 subtype was compared to low-risk groups defined by discretization of Prolaris-like or OncotypeDX-like scores, and to low-risk subtypes identified through the reproduction of Irshad or Proveri computational methods. To define low risk groups using Prolaris-like and OncotypeDX-like scores, an optimal cut-off value was computed for each score to discriminate patients who had a biochemical recurrence from patients who did not recur biochemically. Low risk patients subtyping was then achieved by identifying tumor samples with a Prolaris-like score below 8 or with an OncotypeDX-like score below 30. Hazard ratios for the five definitions of low risk groups refer to the relative risk of biochemical recurrence in a multivariate cox model including ISUP group (1-2 vs 3-4), tumor stage (T2 vs T3-T4), and PSA level (below or above 4 ng/mL) from 708 tumor samples.

EXAMPLES

The present invention is further illustrated by the following examples.

Example 1: Analysis of mRNA Expression and DNA Methylation Reveals 3 Distinct Prostate Adenocarcinoma Molecular Subtypes Materials and Methods Patients and Samples Included in CIT Cohort The CIT (Cartes d'Identité des Tumeurs®) retrospective cohort study included 130 patients with localized PCa from CHU Poitiers, CHU Pointe à Pitié/abymes, GH Pitid-Salpétrière, CHU Brest, CHU Lille and Tenon hospital. All patients have providedwritten informed consent consistent with local Research Ethics Board guidelines. The study protocol (CeRePP-PROGENE) was approved by the CPP Ile-de-France IV Institutional Review Board (IRB00003835).

A total of 195 samples were included in the CIT cohort: 130 tumors and 65 normal adjacent samples. All tumor specimens were centrally reviewed by an expert urological pathologist. Biochemical relapse was reported when patient PSA levels rose above 0.2 ng/mL followed by another increase after radical prostatectomy.

Sample details are given in Table 3.

TABLE 3

Clinical characteristics of S1, S2 and S3 tumor subtypes (CIT + TCGA cohorts)

|  |  | S1 (n = 169) | S2 (n = 111) | S3 (n = 216) |
|---|---|---|---|---|
| ISUP group (Gleason Score) Chi2 p-val: $6.02 \times 10^{-26}$ | 1 (GS 6) | 5 (3%) | 36 (32.4%) | 28 (13%) |
|  | 2 (GS 3 + 4) | 20 (12.2%) | 54 (48.6%) | 48 (22.3%) |
|  | 3 (GS 4 + 3) | 41 (25%) | 13 (11.7%) | 55 (25.6%) |
|  | 4-5 (GS 8-9) | 98 (59.8%) | 8 (7.2%) | 84 (39.1%) |
| Tumor stage Chi2 p-val: $4.63 \times 10^{-14}$ | T2 | 34 (20.9%) | 75 (68.2%) | 95 (44.4%) |
|  | T3-T4 | 129 (79.1%) | 35 (31.8%) | 119 (55.6%) |
| Age Nova p-val: 0.00582 | Mean | 61.4 | 59.7 | 62.2 |
|  | Median | 62 | 60 | 63 |

Procedures

CIT samples were profiled on mRNA expression arrays (E-MTAB-6128), DNA methylation arrays (E-MTAB-6131), and SNP arrays (E-MTAB-6126). Profiling protocols are detailed below.

The Cancer Genome Atlas (TCGA) data were downloaded from Broad GDAC Firehose (doi:10.7908/C11G0KM9).

We used an in silico method to estimate the proportion of tumor cells in each sample that was profiled on Illumina HumanMethylation450 array. To identify molecular subgroups of prostate adenocarcinoma tumors, we performed classifications of mRNA expression data and DNA methylation data using a consensus clustering method.

To assess the validity of our subtypes, we used the same approach on TCGA mRNA and methylation data and computed Pearson's correlations between the mean profiles of resulting CIT and TCGA subtypes.

An mRNA-based predictor (detailed below) was built to predict tumor subtypes in 4 independent public datasets and measure their association with prognosis.

DNA and mRNA Extraction and Preparation

DNA and total RNA were simultaneously extracted from 179 frozen samples using a modified protocol of AllPrep DNA/RNA Kit from Qiagen. Two steps were modified: 1.5 volume of ethanol 100% was added to the RNA flow-through during the first step of RNA purification, and the column was washed with RWT buffer instead of RW1 buffer. All other steps were followed according to the manufacturer's protocol.

Phenol/Chloroform standard protocol and miRNeasy Mini Kit from Qiagen were used to extract DNA and RNA from the 16 remaining frozen samples. The QIAzol lysis buffer was replaced by Trizol buffer+10% guanidine thiocyanate in the lysis step of the RNA extraction protocol.

DNA and RNA quality controls were performed according to CIT program protocols.

mRNA Expression Profiling mRNA expression profiling was carried out by the IGBMC Microarray and Sequencing platform. 101 tumor samples and 40 adjacent normal samples were profiled on Affymetrix GeneChip Human Gene 1.0 ST arrays according to Affymetrix recommendations. We used RMA (Robust Multi-array Average) method from Bioconductor affy package to compute probe set signal intensities and normalize the data.

DNA Methylation Array Processing

We used Illumina Infinium HumanMethylation450 Beadchips to study DNA methylation in 130 tumor samples and 65 adjacent normal samples. Hybridization was carried out by Integragen SA (Evry, France) according to the manufacturer's recommendations. Illumina GenomeStudio software was used to compute beta values and detection p-values for each methylation locus. Since our cohort included both Caucasian patients and patients from the French Caribbean sharing African origins, we used the CpG annotation from Chen et al. (2013. *Epigenetics*. 8(2):203-9) to exclude polymorphic sites between African and European population for further analysis.

SNP Array Processing

Illumina HumanOmniExpress-12v1 arrays were used to analyze DNA copy number from 130 tumor samples. Hybridization was carried out by Integragen SA (Evry, France) according to the manufacturer's recommendations. Illumina BeadStudio software was used to normalize raw fluorescent signals and generate log R ratio (LRR) and B allele frequency (BAF).

We used tQN normalization procedure (Staaf et al., 2008. *BMC Bioinformatics*. 9:409) to correct the bias between the two dyes used in Illumina assays. Genomic profiles were segmented using the circular binary segmentation algorithm (Venkatraman & Olshen, 2007. *Bioinformatics*. 23(6):657-63) and smoothed values of LRR and BAF were assigned accordingly. Allele-specific number of each segment was determined according to GAP (Genome Alteration Print) method (Popova et al., 2009. *Genome Biol*. 10(11):R128). The resulting segmented files were pooled with TCGA segmented files before applying GISTIC2.0 algorithm within each subtype.

Estimation of Tumor Content from DNA Methylation Data

We used the Python tool "InfiniumPurity" developed by Zhan et al. (2015. *Bioinformatics*. 31(21):3401-5) to get an estimation of the proportion of tumor cells in each sample that was profiled on Illumina HumanMethylation450 array. We followed the workflow described in their publication in order to identify reference sets of hypomethylated and hypermethylated CpG positions when comparing pure normal samples with tumor samples in the CIT cohort. We selected the CpGs using cut-offs set to respectively 0.005 for the minimum variance in tumor samples and $1 \times 10^{-24}$ for the maximum Wilcoxon p-value in tumor versus normal samples comparison. The tumor content of all samples with a methylation profile from CIT and TCGA cohorts was then estimated by running InfiniumPurity tool using our selection of reference CpGs.

Consensus Clustering of mRNA and DNA Methylation Data.

All consensus clustering analyses were carried out using the Bioconductor ConsensusClusterPlus R package. For mRNA data (resp. DNA methylation data) classification, we selected the probe sets with a median absolute deviation>0.3 (resp. 0.2) to determine the consensus partitions into K clusters (for K varying from 2 to 8). Consensus clustering computations were performed using Pearson's dissimilarity for the distance metric, Ward's linkage method, and 1000 (500 for DNA methylation data) resampling iterations of hierarchical clustering. Default values were maintained for the remaining parameters. To determine the optimal number of clusters, we used the cumulative distribution functions (CGFs) of the consensus matrices and considered both the shape of the functions and the area under the CDF curves, as previously described (Wilkerson & Hayes, 2010. *Bioinformatics*. 26(12):1572-3).

Results

We studied a series of 130 primary prostate adenocarcinoma samples and 65 adjacent normal prostate samples referred henceforth as the CIT cohort. These samples were all profiled on both DNA methylation and SNP arrays, and 101 of them were also profiled on mRNA arrays. In order to avoid the bias from normal cells contamination and thus define "pure" molecular subtypes of prostate tumors, we first restricted our analysis to 63 samples containing more than 50% of tumor cells as estimated through their DNA methylation profiles (FIG. 1). Consensus hierarchical clustering of mRNA expression and DNA methylation data were remarkably consistent and revealed two stable methylation subgroups (M1 and M2), which could further be subdivided into three stable subgroups with distinct transcriptomic profiles (S1, S2, S3).

Figure 2:
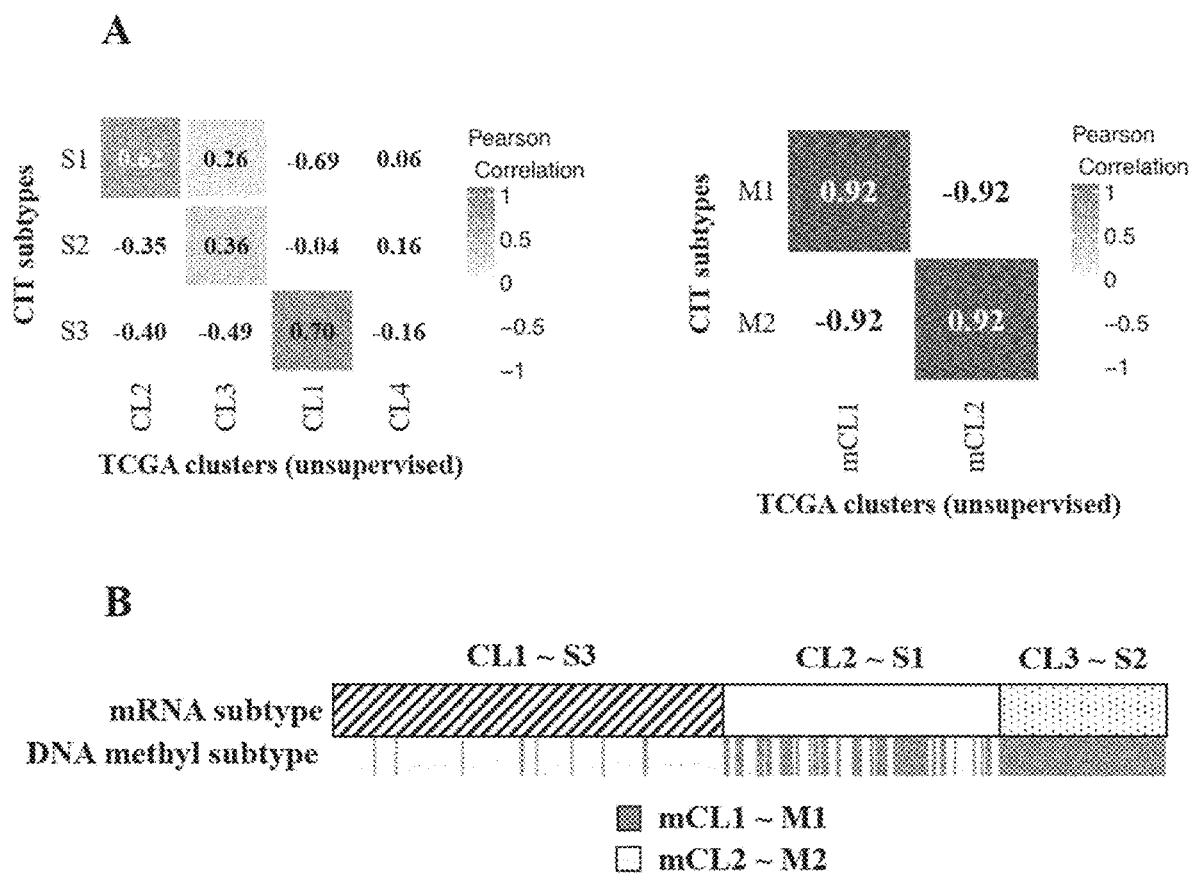
FIG. 2 is a set of graphs illustrating the validation of CIT subtypes in TCGA cohort. (A) Comparison of unsupervised classification results from TCGA data and CIT subtypes using mRNA expression (left panel) and DNA methylation data (right panel). Unsupervised clustering was performed with ConsensusClusterPlus R Package. Similarity between the 4 (resp. 2) unsupervised TCGA mRNA (resp. DNA methylation) subtypes and the 3 (resp. 2) CIT mRNA (resp. DNA methylation) subtypes was assessed by computing each subtype centroids and measuring pairwise Pearson correlations. (B) Correspondence between TCGA mRNA subtypes and DNA methylation subtypes.

We further validated this classification system using the same approach on public data from TCGA Prostate Adenocarcinoma (PRAD) cohort. We performed a de novo classification of mRNA and DNA methylation data using only samples with more than 50% of tumor cells. Three of the four resulting mRNA classes had a good correlation with the CIT mRNA subtypes (Pearson's correlation ranging from 0.36 to 0.70; FIG. 2A), thereby suggesting the existence of our three subtypes in the TCGA cohort.

Similarly, the two DNA methylation subtypes revealed in TCGA cohort were highly correlated to the CIT DNA methylation subtypes (Pearson's correlation=0.92; FIG. 2A).

Moreover, just as observed in the CIT series, we found a significant association between the three correlated TCGA mRNA subtypes and the two DNA methylation subtypes (Fisher test p-value<10-53), thereby reinforcing the classification system revealed from our data (FIG. 2B).

Example 2: Comprehensive Molecular Characterization of S1, S2 and S3 Subtypes

Materials and Methods

Identification of subtype specific transcriptomic changes and differential DNA methylation We used Bioconductor limma package (Richie et al., 2015. *Nucleic Acids Res.* 43(7):e47) to search for differentially expressed genes between subtypes in CIT and TCGA datasets. Four comparisons were performed for each dataset:

S1 tumors/non-S1 tumors,
S2 tumors/non-S2 tumors,
S3 tumors/non-S3 tumors, and
S1-tumors/S2-tumors.

For gene sets enrichment analysis, we performed hypergeometric tests between gene-set members and the top 400 most differentially expressed genes (top 200 upregulated genes and top 200 downregulated genes) in each comparison (adjusted p-value<0.05, genes were ordered according to their fold-change for each comparison). Gene-set member lists were retrieved online from MSigDB, GO and SMD databases. Additional gene lists were added to this main set on the basis of specific publications of interest (authors' names are included in the corresponding gene set names). We used Stouffer's Z-score method to combine enrichment p-values obtained on CIT and TCGA datasets and further considered gene sets with an associated Stouffer p-value<0.05.

Single sample GSEA was performed for each gene set in both CIT and TCGA cohort using Bioconductor GSVA package (Hanzelmann et al., 2013. *BMC Bioinformatics.* 14:7). The resulting matrices were scaled and centered by gene sets in order to be pooled for graphical representation.

The limma package was also used to search for differentially methylated CpGs between the two methylation subtypes M1 and M2, in both CIT and TCGA datasets. We used Stouffer's Z-score method to combine the resulting p-values and selected CpG positions with Stouffer's p-value<0.05.

Transcriptomic Predictor of S1, S2 and S3 Subtypes

We selected CIT tumor samples with more than 50% estimated tumor content as well as normal samples with less than 20% tumor content in order to build an mRNA based predictor of tumor subtypes S1, S2, S3, and normal-like samples (tumor samples with too few tumor content to be labelled as tumor material). Using these carefully selected samples, we selected the top more specific genes of each of these four transcriptomic groups among genes that were common to all the independent datasets further analyzed.

Limma was used to identify differentially expressed genes and AUC measures were calculated for each gene and each group to sort genes according to their predictive power. A total of 847 gene features were selected and the mean profile of each group was computed for these features after centering the data by gene. The resulting mean profiles (or centroids) were used to predict tumor subtypes in 4 independent public datasets: RNA-seq data from 497 tumor samples from TCGA cohort (2015. Cell. 163(4):1011-25), Affymetrix exon array data from 131 tumor samples from Taylor et al. (2010. *Cancer Cell.* 18(1):11-22), Illumina expression data from 219 tumor samples from Ross-Adams et al. (2015. *EBioMedicine.* 2(9):1133-44), and Affymetrix human transcriptome array data from 56 tumor samples from Fraser et al. (2017. *Nature.* 541(7637):359-364).

For each dataset, the mRNA data was first scaled by gene before computing Pearson's correlations of each sample profile with the centroids. A sample was then assigned to the group whose centroid was the more correlated with its profile. A supplementary deconvolution method described below was then used to refine the predictions for samples with a low cellularity.

Deconvolution Method to Re-Assign Subtypes to Low Cellularity Samples.

For the CIT cohort, we defined as "core" tumor samples representing each subtype the samples with at least 50% of tumor cells whose mRNA profile had a Pearson's correlation>0.4 with the metagene mean profile for their subtype. Those samples, together with normal samples, were then used to build a linear model that was fit to each tumor sample using quadprog package. Each tumor sample $T_i$ was then modelled as $$T_i = w_{1,i}S1 + w_{2,i}S2 + w_{3,i}S3 + w_{N,i}N + \varepsilon_i,$$

where $\{w_{1,i}, w_{2,i}, w_{3,i}, w_{N,i}\}$ are the weights of tumor $T_i$ associated with S1, S2, S3 subtypes and N (for Normal tissue), and si is the residual error.

Those weights estimate the proportion of each cell population contained by the tumor sample under the hypothesis that each tumor sample is a mix of the four populations considered in the model. We then re-assigned the samples according to the highest weight. Only samples that were not yet assigned to a subtype and whose top weight was not the normal weight were re-assigned to one of S1, S2 or S3 subtype.

For the four public cohorts, we defined as "core" tumor samples representing each subtype the samples whose mRNA profile had a Pearson's correlation>0.4 with the metagene mean profile for their subtype. The approach described above was similarly applied to each public dataset to re-assign samples after initial predictions results.

Results

We used pooled data from both CIT and TCGA cohorts to further characterize S1, S2 and S3 subtypes using clinical data, as well as mRNA, copy number and mutation data (data not shown). S1, S2 and S3 labels were assigned to TCGA samples using a transcriptomic predictor described in the "materials and methods" section. The analysis of mRNA and copy number data revealed a strong association of the subtypes with the TMPRSS2/ERG fusion (Fus+). S1 and S2 subtypes strongly expressed the transcriptomic fusion signature as defined in Setlur et al. (2008. *J Nat Cancer Inst.* 100(11):815-25), and the typical losses of TMPRSS2 genomic locus were found in both subtypes. On the other hand, S3 tumors showed neither transcriptomic nor genomic marks of the fusion (Fus−).

Figure 3:
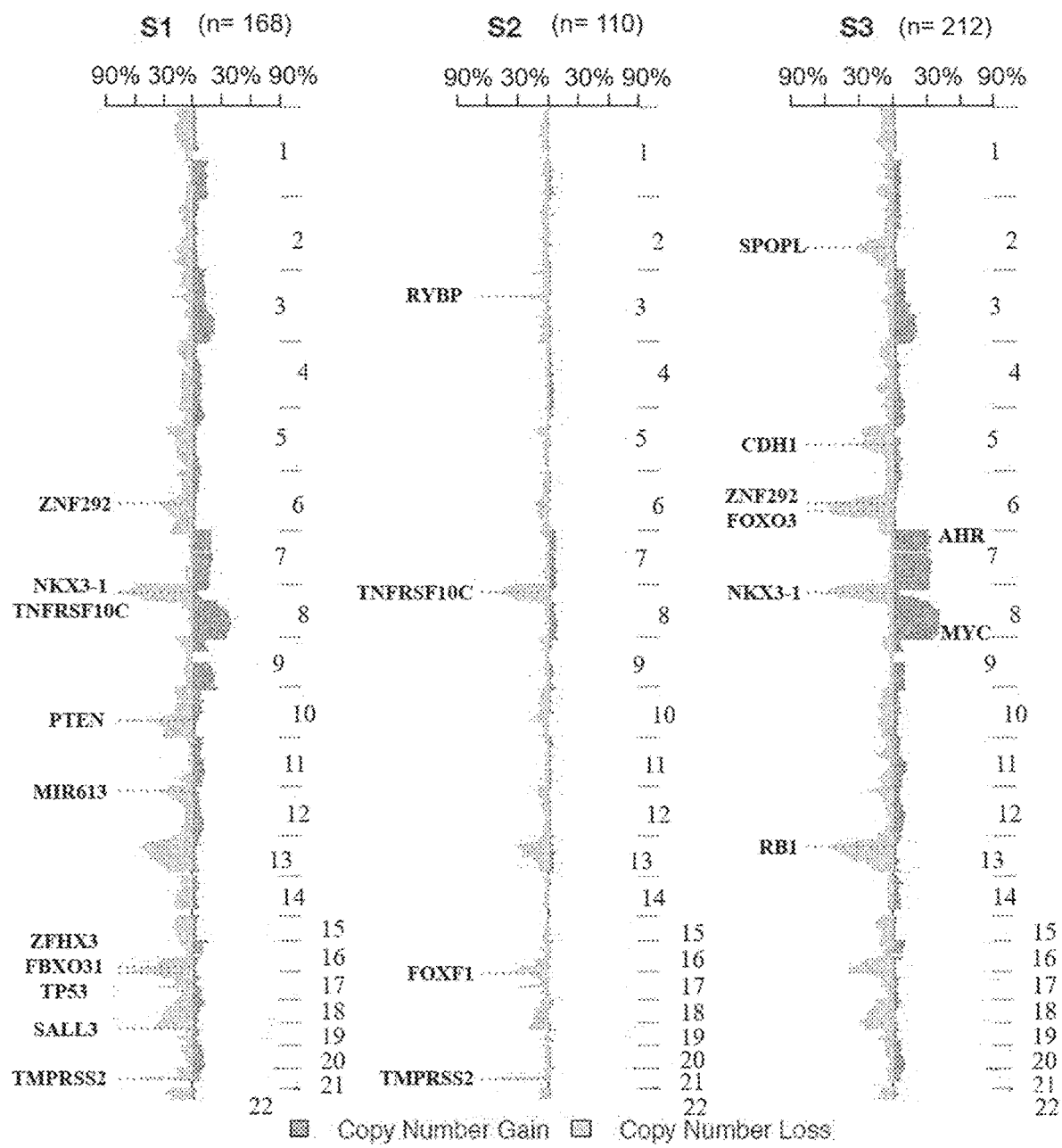
FIG. 3 is a set of graphs showing the copy number profile of S1 (left panel), S2 (middle panel) and S3 (right panel) subtypes. The copy number profiles of 490 tumor samples grouped by subtype was analyzed. GISTIC2 was used to identify regions that were significantly gained or lost in each subtype and the names of putative candidate genes targeted by the significant genomic events were reported graphically.
Figure 4:
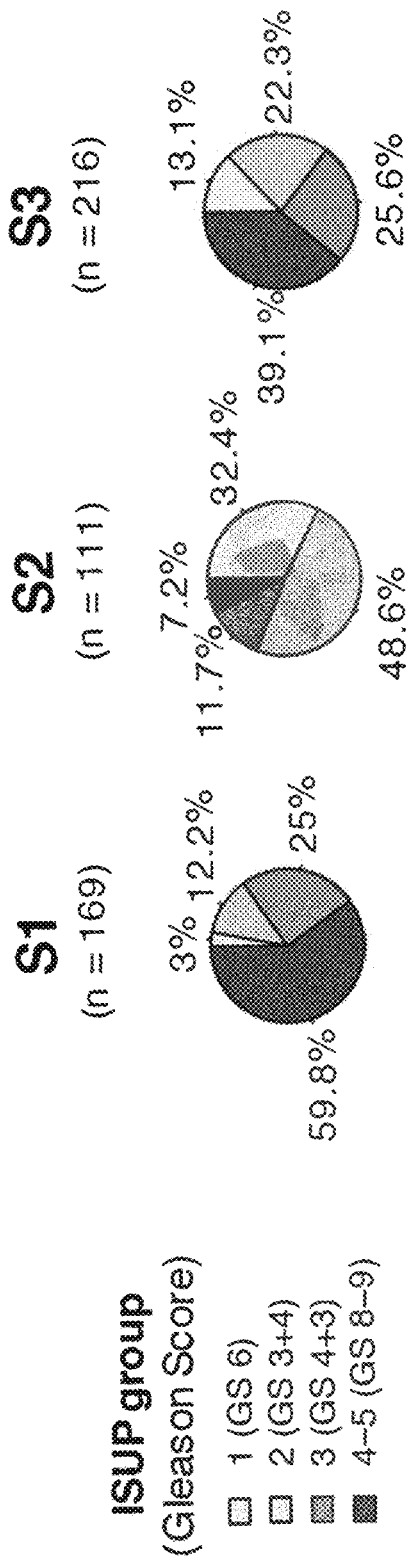
FIG. 4 is a set of graphs showing the clinical and molecular characterization of tumor subtypes using CIT and TCGA cohorts. ISUP groups were distributed within subtypes. 496 samples from CIT and TCGA cohorts were assigned one of S1, S2 or S3 subtypes. The pies show the proportion of ISUP groups within each subtype.

While sharing the Fus+ molecular pattern, S1 and S2 subtypes showed distinct clinical and genomic properties. 85% of S1 samples fall into ISUP group 3 or higher and were characterized by numerous significant losses of genomic loci (FIG. 3). This subgroup was particularly associated with frequent deletions of PTEN (67%). Mutations in TP53 gene were frequently found in S1 tumors (22%) and significantly associated with this subtype (Fisher p-value<10-4). Unlike S1 tumors, S2 tumors were enriched in low Gleason scores (32.4% of ISUP group 1) and harbored few genomic gains and losses (FIG. 4). However, RYBP genomic locus (3p13) was more frequently lost in S2 tumors (38%) compared to S1 (24%) (Fisher p-value=0.04), and the rare mutations within gene TMPRSS2 were only found in S2 tumors (5%, Fisher p-value=0.003). Consistent with the differences in their genomic profiles, S1 tumors transcriptomic profile showed a clear inactivation of p53 and PTEN pathways as compared to S2 tumors, as well as higher proliferation signals and a diminished androgen response.

S3 subtype perfectly overlapped the TMPRSS2/ERG Fusion negative status (Fus−). Our analysis confirmed the previously reported associations of Fus− tumors with SPOP (28%) and FOXA1 mutations (15%) as well as frequent losses of chromosome arms 2q, 5q, and 6q (Barbieri et al., 2012. *Nat Genet.* 44(6):685-9). CHD1 losses were found in 37% of S3 tumors. The loss of ZNF292 was observed in 60% of S3 tumors, therefore ranking as the most frequently deleted locus in those tumors. As for chromosome arm 2q, we identified a deletion peak encompassing SPOPL in 31% of S3 tumors. Finally, we found that S3 tumors were also significantly associated with mutations of KDM6A (Fisher pvalue=0.01) and BRAF (Fisher p-value=0.02) which are both related to epigenetic modifications in cancers.

Figure 5:
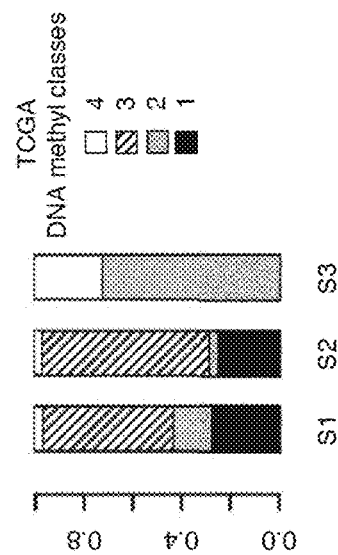
FIG. 5 is a set of histograms showing the relation between CIT subtypes and published TCGA subtypes. An mRNA-based predictor was used to assign CIT subtypes to TCGA samples and their distribution was compared relatively to TCGA subtypes published in 2015. S1 and S2 tumors are almost exclusively classified as TMPRSS2/ERG fusion positive (ERG, ETV1, ETV4 or FLI1 subtypes), while tumors carrying SPOP or FOXA1 mutations are all assigned to S3 subtypes (left panel). S1 and S3 subtypes are highly consistent with classes 1 and 2 of TCGA transcriptomic classification whereas TCGA class 3 is mainly represented in S2 subtype (middle panel). As for DNA methylation profiles, we confirm a dichotomy between S3 (M2) tumors matching up with DNA classes 2 and 4 on one side, and S1/S2 (M1) tumors both falling into classes 1 and 3 (right panel).
Figure 5:
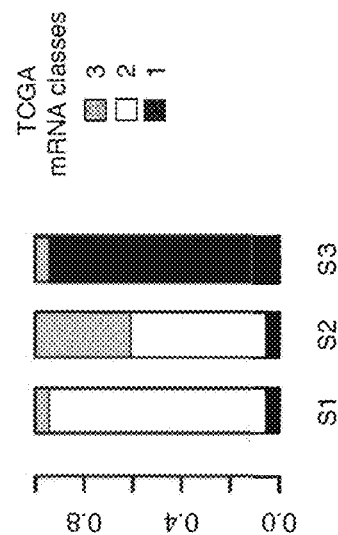
Figure 5:
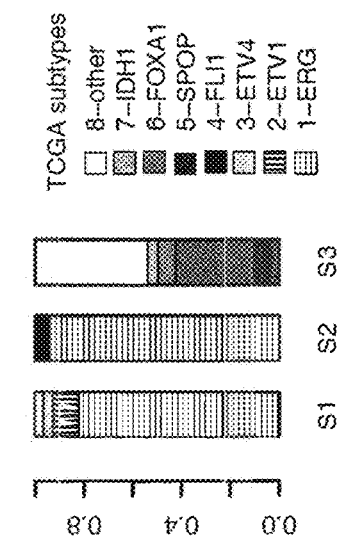

We compared the three-class CIT system with the classification results published by TCGA in 2015 (Cancer Genome Atlas Research Network, 2015. *Cell.* 163(4):1011-25) and found it rather consistent with the published subtypes and consensus classes (FIG. 5).

Example 3: S2 Subtype is Strongly Associated with the Absence of Biochemical Recurrence after Radical Prostatectomy in 4 Distinct Cohorts Materials and Methods Statistical Analysis All association strengths between molecular subtypes and other categorical variables were assessed with Fisher exact tests or Chi-square tests. Associations with continuous variables were evaluated with either Kruskal-Wallis tests or ANOVA. Relapse-free survival analyses were performed on patients from 5 independent cohorts considering biochemical recurrence (BCR) as the relapse event. We selected patients whose tumor had been assigned one of S1, S2, and S3 subtypes and removed patients with missing clinical data. We built univariate and multivariate Cox models based on molecular subtyping and clinical risk factors, stratified on each cohort (separate baseline hazard functions were fit for each strata). We constructed Kaplan-Meier curves and used log-rank tests to compare patient groups. All statistical or bioinformatics analyses were performed with version 3.3.2 of R software environment.

Results

Figure 6:
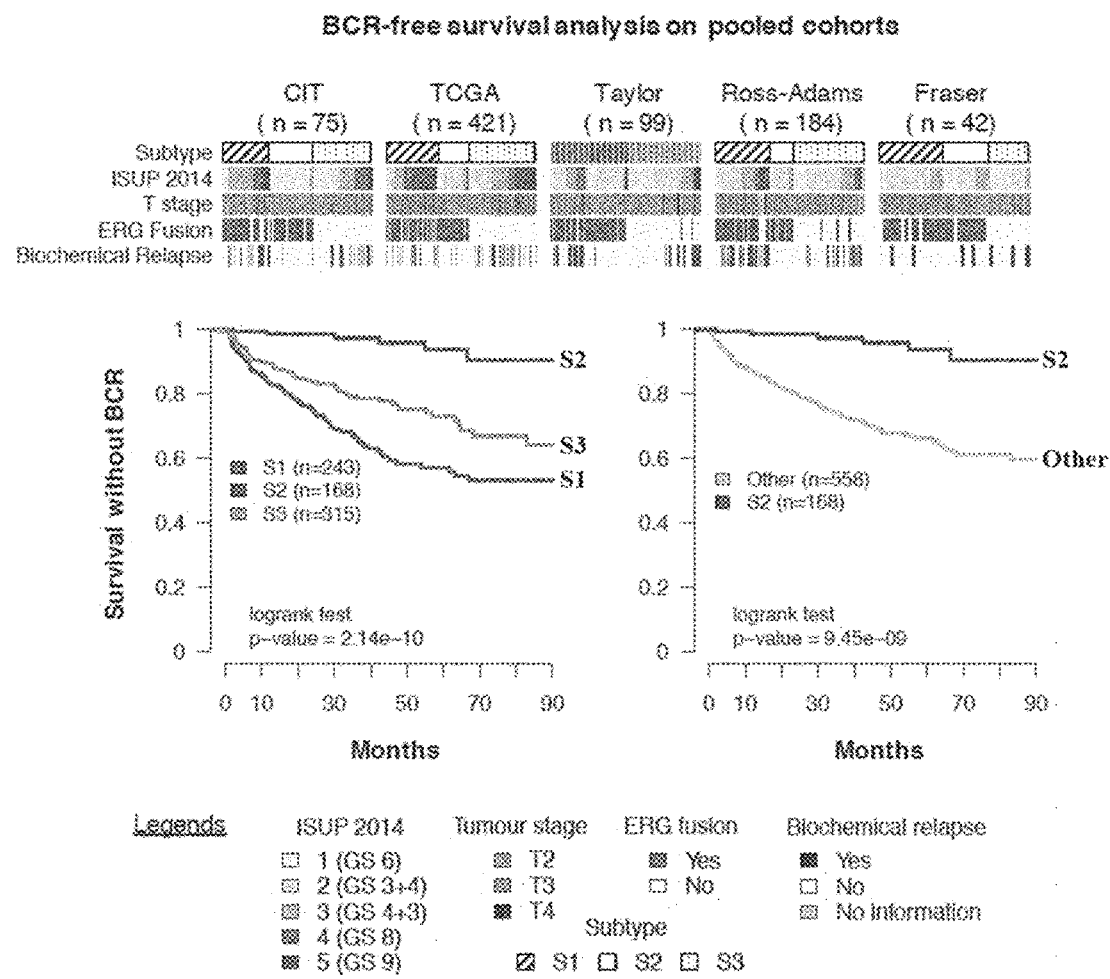
FIG. 6 is a set of graphs showing the association of molecular subtypes with patient prognosis. Meta-analysis of survival without biochemical recurrence (BCR) was assessed in five cohorts used to study the association of CIT subtypes with prognosis. The clinical characteristics associated with tumor samples that were used to predict S1, S2 or S3 subtypes in each cohort are reported on this figure. TMPRSS2/ERG fusion status was assigned according to the transcriptomic signature from Setlur et al. (2008. *J Natl Cancer Inst.* 100(11):815-25). Kaplan-Meier plots show the evolution of patients' survival without BCR, stratified by molecular subtypes. The data from 726 patients with available clinical follow-up data from the five cohorts described were pooled, and Kaplan-Meier curves estimating survival without BCR were generated. We used log-rank tests to assess the significance of differences between survival distributions of patients when comparing S1, S2, and S3 subtypes (left panel) or S2 relatively to S1 and S3 subtypes (right panel).

We found it noteworthy that within patients having an S2 tumor, none had had a biochemical recurrence (BCR) in CIT cohort and only one had recurred in TCGA cohort. In order to assess the significance of this association, we predicted S1, S2 and S3 subtypes in 3 additional cohorts with available mRNA and clinical data (Taylor et al., Ross-Adams et al. and Fraser et al., cited above) and performed a BCR-free survival analysis on the pooled cohort of 821 patients with primary prostate adenocarcinoma (FIG. 6).

Figure 7:
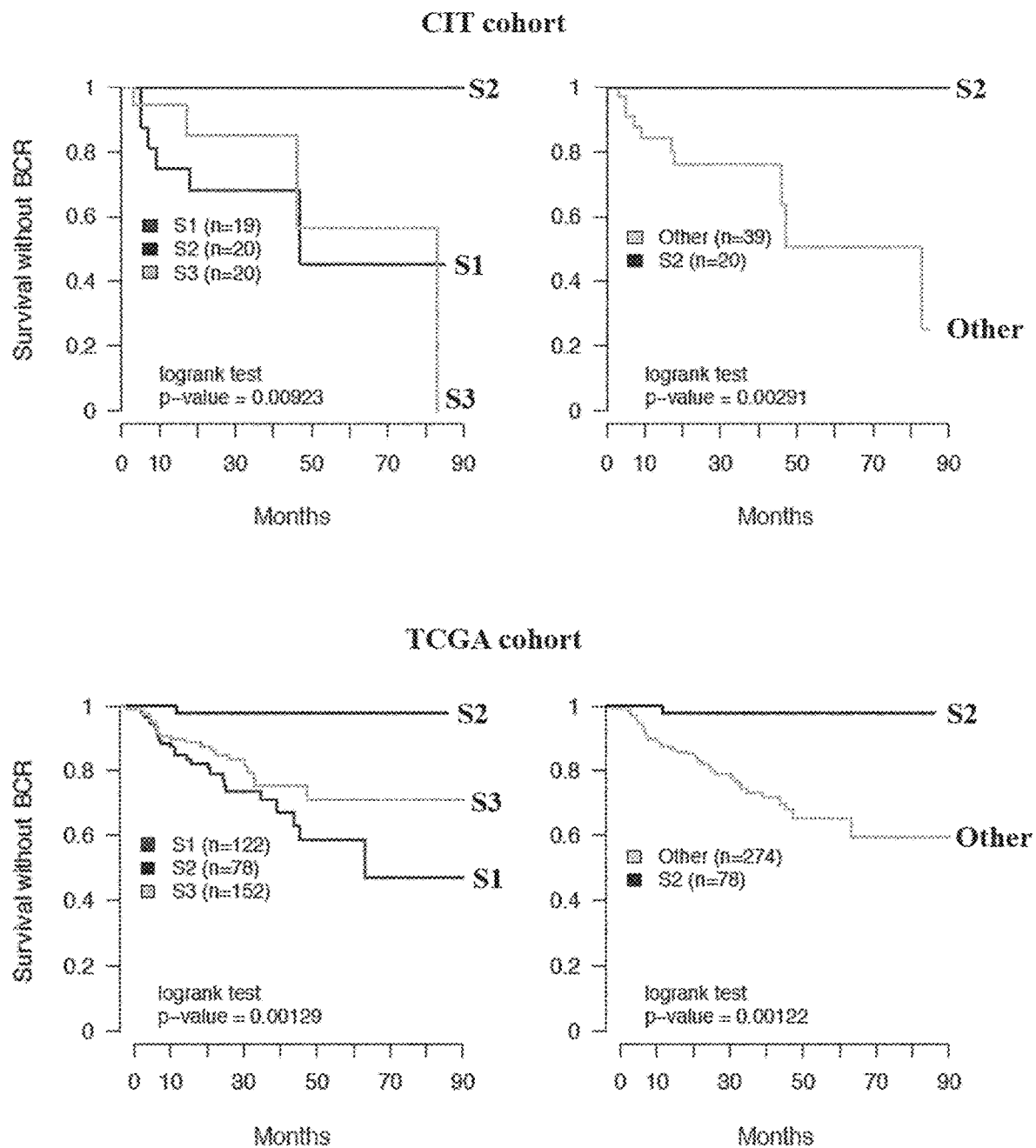
FIG. 7 is a set of four graphs showing patient survival without biochemical recurrence in CIT and TCGA cohorts.

Subtypes clinical features and association with ERG fusion in each cohort were consistent with the features observed in the CIT discovery cohort. The pooled analysis of patients from the 5 cohorts revealed a strong and significant association of CIT subtypes with BCR free survival (log-rank test p-value<$10^{-9}$), particularly for S2 subtype which was strongly associated to survival without BCR (log-rank test p-value<$10^{-8}$). CIT subtypes were more predictive of BCR-free survival than any of the classification systems published by TCGA, Taylor, and Ross-Adams (FIG. 7).

Multivariate analysis including ISUP class, tumor stage, and PSA confirmed that S2 subtype was an independent prognostic factor (likelihood test p-value=$1.11 \times 10^{-4}$, Table 4). Taken alone, S2 vs non S2 subtyping approach achieved a positive predictive value of 95.83% for the absence of BCR, which was the best score among all significant predictive factors analyzed.

TABLE 4

Multivariate recurrence-free survival analysis using Cox's regression model. Regression analysis was performed on 708 samples with complete annotations for the included factors, and stratified on cohorts. For each predictive factor, we reported the hazard ratio (HR) associated with biochemical recurrence, as well as the corresponding confidence intervals and likelihood test p-values. We also computed Fisher exact test p-values and Positive Predictive Values (PPV) associated with each factor used to predict the absence of biochemical recurrence.

| Predictive factor of survival without BCR | Hazard ratio | Confidence interval | P (likelihood) | Association with absence of BCR P (Fisher test) | PPV |
| --- | --- | --- | --- | --- | --- |
| Subtype: S2 | 0.27 | 0.12-0.58 | $8.81 \times 10^{-4}$ | $3.91 \times 10^{-11}$ | 95.86% |
| ISUP: 1-2 | 0.28 | 0.18-0.41 | $2.72 \times 10^{-10}$ | $4.28 \times 10^{-10}$ | 69.89% |
| T stage: T2 | 0.38 | 0.25-0.57 | $4.13 \times 10^{-6}$ | $6.31 \times 10^{-10}$ | 89.60% |
| PSA level <4 ng/mL | 0.68 | 0.30-1.29 | 0.202 | $9.20 \times 10^{-5}$ | 73.76% |

Example 4: S2 Subtyping is a Promising Predictive Tool for Suspected Indolent Prostate Adenocarcinoma Materials and Methods Comparison of S2 Subtyping to Other Prognostic Molecular Approaches We compared the prognostic power of S2 subtyping to Prolaris® Test, OncotypeDX® Genomic Prostate Score, Irshad et al prognostic groups, and Proveri Inc prognostic biomarkers.

For Prolaris test, we used the 31 genes listed in the publication from Cuzick et al. (2011. *J Clin Oncol.* 29(32): 4273-8) to compute a continuous score over the tumor samples for each of the five datasets included in the study. For a given dataset, we kept the most variant probe sets corresponding to each of the 31 genes, then scaled and centered by gene the resulting mRNA matrix. A Principal Component Analysis (PCA) was performed on the matrix, with genes as variables, and the projection of each sample on the first component (component capturing the greatest proportion of variance from the data) was defined as a Prolaris-like score.

For OncotypeDX score, we used the 17 genes from Knezevic et al. (2013. *BMC Genomics.* 14:690), and transposed to array signals the analytical computation described in the publication to calculate sample scores on each dataset independently. For a given dataset, we kept the most variant probe sets corresponding to each of the 17 genes, then scaled and centered the data by gene. We used mRNA signals instead of Cp, and the scaling step was adapted as follow to the resulting data range and performed only after aggregating the 5 cohorts: $100 \times GPS_u - 100 \times (\max(GPS_u) - 1)$. After this scaling step, we obtained scores ranging from 0 to 100.

To define prognostic groups of low aggressive cases using the computed Prolaris and OncotypeDX scores, we discretized both scores after determining an optimal cut-off on each cohort based on the corresponding BCR-free survival data.

To determine risk groups as described in Irshad et al. (2013. *Sci Transl Med.* 5(202):202ra122), we used the approach described in the publication taking each dataset independently. For a given dataset, we selected the most variant probe sets for each of the genes FGFR1, PMP22 and CDKN1A and performed a k-means clustering on the data from these three genes. We used kcca function from R flexclust package with kmeans++ initialization. The cluster with the lowest number of relapse event was then defined as the "low risk group".

For the predictions with Proveri Inc prognostic biomarkers, we used the in silico approach described in Jia et al. (2012. *PLoS One.* 7(8):e41371). We built a predictor using R pamr package on the 15 genes and data from the 18 patients (9 low risk and 9 high risk) of dataset GSE8218 as mentioned in the publication. For the 3 genes with several probe sets, we kept the most variant probe set. Data was quantile normalized then scaled and centered before building the predictor. We used this predictor and the pamr.predict function to define low risk and high risk groups in each dataset once the same normalization steps had been performed (quantile normalization, centering and scaling), and the most variant probe sets had been selected for each gene.

Results

We compared the predictive power of S2 subtype with four molecular approaches, including two popular mRNA-based prognosis tools associated to BCR: Prolaris® Test and OncotypeDX® Genomic Prostate Score. These tools are used by clinicians to better identify patients with aggressive tumors from patients who are not likely to progress. We used the published data from Cuzick and Knezevic to assign a Prolaris-like and OncotypeDX-like scores to the 821 samples and compared the predictive power of these scores with S2 subtyping.

Figure 8:
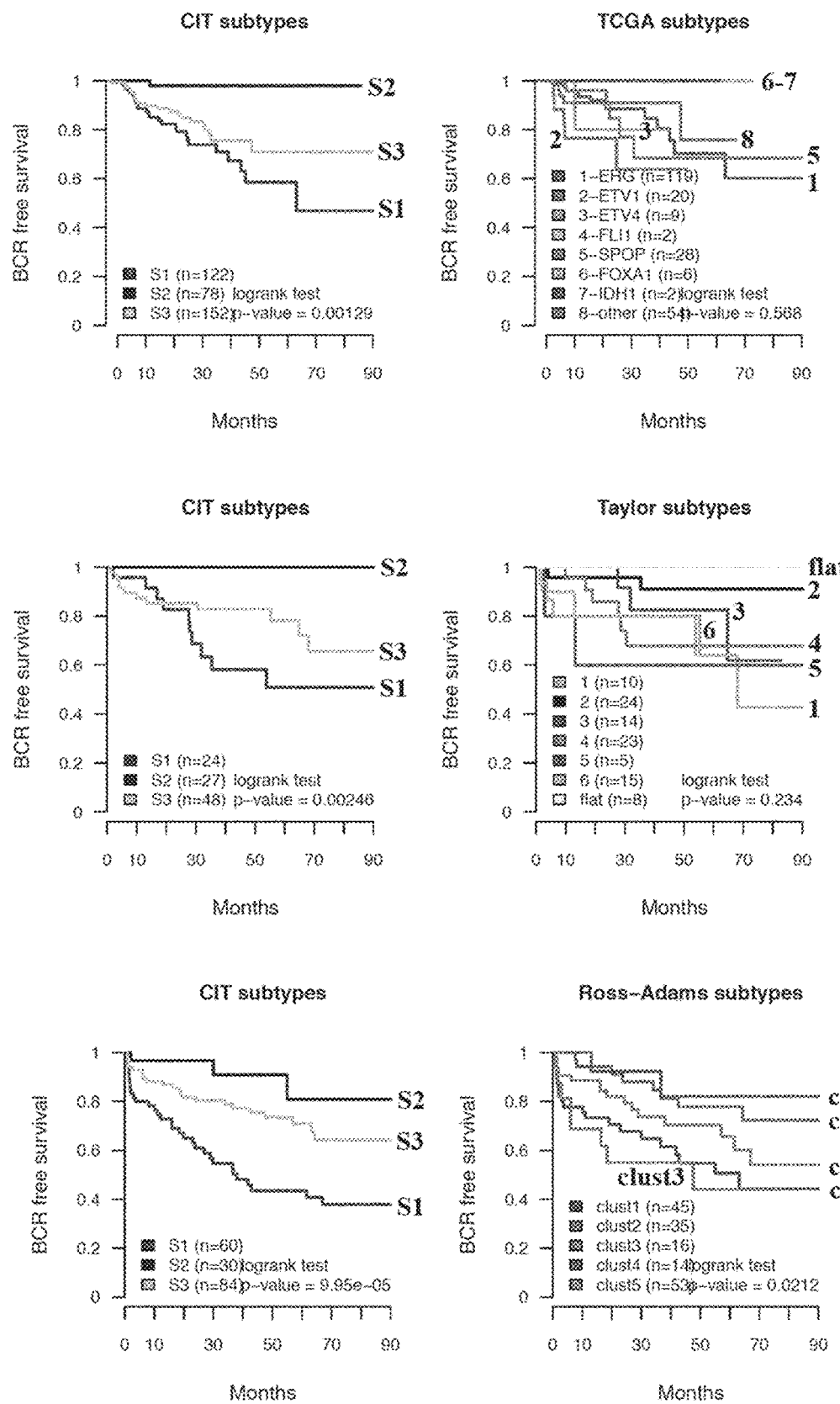
FIG. 8 is a set of six graphs showing the association with prognosis using CIT subtypes or original classification system in TCGA, Taylor and Ross-Adams cohorts.
Figure 9:
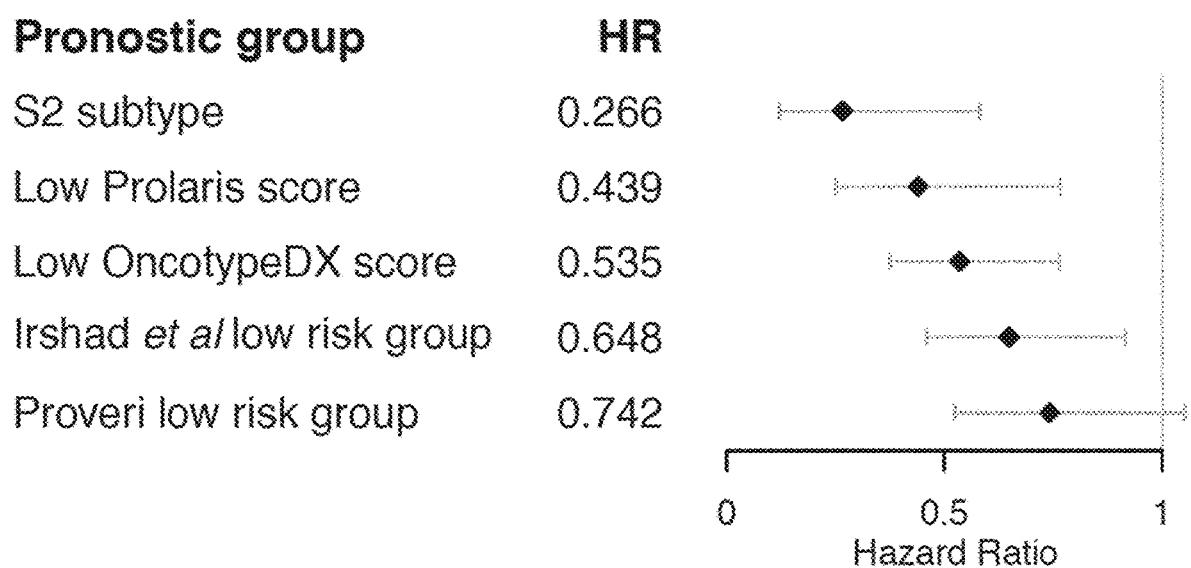
FIG. 9 is a diagram showing the prognostic power of S2 subtyping relatively to other known molecular approaches.

As expected, we observed that S2 subtype was significantly associated with lower Prolaris-like and OncotypeDX-like scores as compared to S1 and S3 subtypes (p-values<10-15; FIG. 8). Both scores were then discretized to define prognostic groups of low aggressive cases. The two other approaches included were the predictions based on Proveri Inc prognostic biomarkers and the molecular signature of Irshad et al, which was precisely designed to identify patients with a non-evolutive disease. For both predictive approaches, we used the same methods that were described in the publications in order to divide tumor samples into low-risk and high-risk groups. Finally, we computed hazard ratios and corresponding confidence intervals associated with the low risk prognostic groups defined with each approach and compared them to S2 subtyping. Once more, S2 subtyping performed the best to identify PCa without BCR, with a smaller BCR-associated hazard ratio than any low risk groups defined with the 4 other approaches (FIG. 9).

Example 5: S2 Subtype can be Accurately Identified with a List of 39 Transcriptomic Markers Materials and Method Evaluation of the 39 Genes Signature Discriminative Power We used R package pamr to build a predictor based on the list of 39 genes given in Table 5. For each of the 5 cohorts (CIT, TCGA, Taylor, Ross-Adams and Fraser), we trained a predictor on two third of the pool of S1 and S2 samples and used it to predict the last third of S1 and S2 samples. We defined specificity as the percentage of actual S1 tumors that were assigned to S1 tumors, and sensitivity as the percentage of actual S2 tumors that were assigned to S2 tumors.

TABLE 5

List of 39 discriminative genes between S1 and S2 subtypes. Differential expression and discriminative power analyses were performed on 5 cohorts (CIT, TCGA, Taylor, Ross-Adams, Fraser) and the 39 genes were selected based on summary statistics from each cohort results. We computed the correlation of each gene with the estimated % of S2 subtype on the samples of the 5 cohorts and report here the median Pearson correlation. In order to identify if these genes were expressed by the tumor or by its microenvironment, we used the data mentioned by Jia et al. to correlate, when available, each biomarker profile with the proportion of stroma, benign prostatic hypertrophy (BPH) and atrophic glands estimated in the dataset (148 samples).

| Gene Symbol | Fold-change E2vE1 | Stouffer p-value E2vE1 | Correlation with % stroma | Correlation with % benign prostatic hypertrophy | Correlation with % atrophic gland |
|---|---|---|---|---|---|
| ANPEP | 0.99 | $5.09 \times 10^{-11}$ | −0.28 | 0.19 | 0.28 |
| AZGP1 | 1.19 | $4.21 \times 10^{-13}$ | −0.36 | 0.32 | 0.26 |
| SLC15A2 | 1.17 | $9.34 \times 10^{-10}$ | −0.32 | 0.32 | 0.19 |
| CD38 | 1.55 | $7.74 \times 10^{-13}$ | −0.25 | 0.29 | 0.15 |
| NCAPD3 | 1.25 | $3.08 \times 10^{-14}$ | −0.54 | 0.17 | 0.12 |
| COL1A2 | −0.82 | $3.20 \times 10^{-10}$ | 0.46 | 0.07 | 0.08 |
| VCAN | −1.01 | $2.26 \times 10^{-17}$ | 0.31 | 0.09 | 0.07 |
| HGD | 0.77 | $3.20 \times 10^{-09}$ | −0.37 | 0.30 | 0.07 |
| COL3A1 | −0.79 | $1.98 \times 10^{-12}$ | 0.30 | 0.04 | 0.06 |
| MGP | −0.78 | $3.74 \times 10^{-11}$ | 0.42 | −0.03 | 0.06 |
| SLC22A3 | 1.14 | $5.79 \times 10^{-13}$ | −0.10 | 0.23 | 0.03 |
| ACADL | 0.89 | $9.69 \times 10^{-13}$ | −0.45 | 0.14 | 0.03 |
| SULF1 | −0.99 | $1.71 \times 10^{-11}$ | 0.52 | −0.04 | 0.02 |
| COL1A1 | −0.85 | $3.20 \times 10^{-14}$ | 0.27 | −0.05 | 0.02 |
| SPARC | −0.67 | $1.49 \times 10^{-13}$ | 0.55 | 0.17 | 0.02 |
| FMOD | 1.06 | $3.28 \times 10^{-11}$ | −0.21 | −0.18 | 0.00 |
| MS4A6A | −0.69 | $1.25 \times 10^{-08}$ | 0.17 | 0.06 | −0.01 |
| THBS2 | −0.93 | $9.75 \times 10^{-15}$ | 0.18 | −0.28 | −0.01 |
| STXBP6 | 0.70 | $1.21 \times 10^{-11}$ | −0.33 | 0.03 | −0.02 |
| COL8A1 | −0.97 | $5.86 \times 10^{-12}$ | −0.03 | −0.06 | −0.04 |
| ANTXR1 | −0.68 | $2.59 \times 10^{-09}$ | 0.40 | 0.20 | −0.05 |
| CXCL14 | −1.32 | $4.04 \times 10^{-13}$ | −0.24 | −0.26 | −0.05 |
| SFRP4 | −1.36 | $4.06 \times 10^{-19}$ | −0.22 | −0.29 | −0.06 |
| CDH11 | −0.73 | $3.04 \times 10^{-10}$ | 0.36 | −0.09 | −0.06 |
| ASPN | −1.40 | $1.13 \times 10^{-13}$ | −0.21 | −0.27 | −0.07 |
| FRZB | −0.76 | $8.33 \times 10^{-07}$ | 0.41 | 0.00 | −0.07 |
| CHRNA2 | 1.06 | $8.74 \times 10^{-17}$ | −0.34 | 0.01 | −0.07 |
| COMP | −1.50 | $3.37 \times 10^{-19}$ | −0.14 | −0.27 | −0.09 |
| ITGBL1 | −0.69 | $6.53 \times 10^{-17}$ | −0.17 | −0.29 | −0.11 |
| KHDRBS3 | −1.17 | $1.31 \times 10^{-14}$ | 0.14 | −0.17 | −0.11 |
| REPS2 | 0.80 | $9.74 \times 10^{-11}$ | −0.66 | −0.35 | −0.16 |
| NOX4 | −0.86 | $7.78 \times 10^{-14}$ | −0.21 | −0.20 | −0.18 |
| AFF3 | 1.05 | $9.09 \times 10^{-10}$ | −0.49 | −0.15 | −0.19 |
| COL10A1 | −1.31 | $4.40 \times 10^{-15}$ | −0.22 | −0.20 | −0.19 |
| FAM3B | 0.96 | $1.77 \times 10^{-05}$ | n.a. | n.a. | n.a. |
| ANO7 | 0.92 | $1.35 \times 10^{-12}$ | n.a. | n.a. | n.a. |
| GPT2 | 0.77 | $8.61 \times 10^{-16}$ | n.a. | n.a. | n.a. |
| CPXM2 | −0.75 | $1.42 \times 10^{-09}$ | n.a. | n.a. | n.a. |
| SFRP2 | −1.01 | $6.92 \times 10^{-11}$ | n.a. | n.a. | n.a. |

Results

We aimed at identifying a set of surrogate biomarkers which could be used clinically to accurately identify S2 tumors, and therefore non-evolutive cases of PCa. TMPRSS2/ERG fusion positive (Fus+) tumors can be detected with either immunohistochemistry (Chaux et al., 2011. *Am J Surg Pathol.* 35(7):1014-20) or even a simple urine based test (Koo et al., 2016. *Sci Rep.* 6:30722), both methods achieving a very high specificity. We therefore focused on biomarkers that could allow the clinician to isolate S2 tumors from S1 tumors. We performed differential expression analyses in the 5 cohorts described earlier and selected the genes that were significantly deregulated between S1 and S2 tumors in at least 4 of the 5 cohorts. 16 (resp. 23) genes were found to be significantly upregulated (resp. down-regulated) in S2 compared to S1 samples (Table 5).

We also checked the prediction power of these 39 genes by building simple linear classifiers and achieved 93% of specificity and 91% of sensitivity (Table 6).

TABLE 6

Potential to discriminate S2 from S1 tumors using the set of 39 genes.

| Subtype | CIT | | TCGA | | Taylor | | Ross-Adams | | Fraser | |
|---|---|---|---|---|---|---|---|---|---|---|
| predicted | S1 | S2 | S1 | S2 | S1 | S2 | S1 | S2 | S1 | S2 |
| S1 | 8 | 0 | 46 | 5 | 7 | 0 | 20 | 1 | 6 | 1 |
| S2 | 0 | 7 | 2 | 25 | 1 | 9 | 2 | 9 | 0 | 3 |

Example 6: S2 Subtypes can be Accurately Identified with Subsets of 18, 15 or 8 Transcriptomic Markers Using 3 algorithm-based approaches on the 5 cohorts (CIT, TCGA, Taylor, Ross-Adams and Fraser) of Example 5, we aimed at identifying a minimal set of biomarkers which could be used clinically to accurately identify TMPRSS2/ERG fusion positive S2 tumors. The same "Materials and Methods" than in Example 5 was used to evaluate the discriminative power of following minimal sets.

A first set comprising 18 genes was identified. This "18-gene signature" comprises the following discriminative genes:

| CHRNA2 | ANPEP | NCAPD3 |
|---|---|---|
| COMP | SFRP4 | FMOD |
| KHDRBS3 | COL3A1 | ACADL |
| SLC22A3 | SLC15A2 | COL1A1 |
| AZGP1 | GPT2 | REPS2 |
| SPARC | ITGBL1 | ANTXR1 |

The prediction power of these 18 genes was evaluated by building simple linear classifiers and achieved:

93% accuracy*,

90% of sensitivity,

94% of specificity,

92% of positive predictive value (true positives), and

93% of negative predictive value (true negatives).

*Accuracy is calculated as the proportion of true results (both true positives and true negatives) among the total number of results.

A second set comprising 15 genes was identified. This "15-gene signature" comprises the following discriminative genes:

| CHRNA2 | AZGP1 | FMOD |
|---|---|---|
| COMP | ANPEP | SLC15A2 |
| NCAPD3 | REPS2 | KHDRBS3 |
| SFRP4 | GPT2 | VCAN |
| SLC22A3 | ACADL | COL1A1 |

The prediction power of these 15 genes was evaluated by building simple linear classifiers and achieved:

92% accuracy,

90% of sensitivity,

93% of specificity,

91% of positive predictive value (true positives), and

93% of negative predictive value (true negatives).

A third set comprising 8 genes was identified. This "8-gene signature" comprises the following discriminative genes:

| CHRNA2 | SFRP4 | MS4A6A |
|---|---|---|
| KHDRBS3 | COMP | ANPEP |
| ANTXR1 | AZGP1 | |

The prediction power of these 8 genes was evaluated by building simple linear classifiers and achieved:

90% accuracy,

87% of sensitivity,

91% of specificity,

88% of positive predictive value (true positives), and

91% of negative predictive value (true negatives).

CONCLUSION

This study proposes a comprehensive molecular classification of prostate adenocarcinoma integrating mRNA expression, DNA methylation and copy number data. Taking into account the high infiltration of normal cells within prostate primary tumors, we could define three molecular subtypes of prostate tumors S1, S2 and S3, showing distinct features at the genomic, transcriptomic, and epigenetic levels. We have shown that our classification is not only consistent with the most recent TCGA classification, but also contains a strong prognostic power that was lacking in the TCGA study. Here, we successfully combined molecular classification and prognosis implications on a large sample of tumors including a new multi-omics cohort and four distinct major PCa cohorts.

Our work shows that the molecular differences between Fus+ subtypes S1 and S2 have significant implications at the clinical level, and therefore highlights the importance of using molecular tests in clinical diagnostic routine to adapt patients medical care. Overtreatment of patients with prostate cancer is unfortunately a medically recognized fact. Medical studies agree that at least 20% of PCa are non-evolutive diseases and that patients could live with it without benefit of immediate radical treatment. Our work suggests that patients with S2 tumors (here, 22% of patients) may correspond to those putative indolent cases who could reasonably be handled with active surveillance rather than undergoing a radical surgery.

We showed that S2 subtyping was a valuable tool to identify patients with an indolent disease, and outperformed the prognostic power of previously published classifications and molecular signatures. Consequently, we propose a list of 39 surrogate markers for S2 subtype for the development of a new molecular test. This list results from the analysis of five independent cohorts of prostate cancer samples whose mRNA expression was measured through five different technologies: Affymetrix HuGene, Affymetrix HumanExon, Affymetrix HTA, Illumina HT12 and Illumina RNA-seq. We therefore assume that this gene list is preserved from common overfitting issues that partly accounts for the lack of successful clinical transfer of previous set of biomarkers.

This significantly prognosis-related set of 39 mRNA markers identified through five distinct cohorts therefore constitutes a robust basis for developing a routine molecular assay to identify S2 tumors which are not likely to evolve to a higher stage of the disease.

From this set of 39 mRNA markers, we aimed at identifying a minimal set of surrogate biomarkers which could easily be used to achieve the same or equivalent prediction power as the full set of 39 markers. In that respect, we have identified 3 minimal sets of biomarkers comprising respectively 18, 15 and 8 mRNA markers out of the 39 disclosed herein. These minimal 18-gene, 15-gene and 8-gene signatures have been evaluated to reach 93%, 92% and 90% of accuracy, respectively. Finally, 6 mRNA markers (ANPEP, AZGP1, CHRNA2, COMP, KHDRBS3 and SFRP4) are found to be shared by the 39-gene, 18-gene, 15-gene and 8-gene signatures, suggesting their leading role in the identification of S2 tumors which are not likely to evolve to a higher stage of the disease.

The invention claimed is:

1. A method for treating prostate cancer in a subject identified as being at low risk of prostate cancer recurrence, comprising:
(1) identifying the subject as being at low risk of prostate cancer recurrence by:
a) providing a sample from said subject,
b) determining the TMPRSS/ERG fusion status in said sample,
c) if said sample is positive for TMPRSS/ERG fusion (Fus$^+$), determining a molecular signature of said sample by measuring the expression level of:
8 prostate cancer markers: ANPEP, ANTXR1, AZGP1, CHRNA2, COMP, KHDRBS3, MS4A6A and SFRP4; or
15 prostate cancer markers: ACADL, ANPEP, AZGP1, CHRNA2, COL1A1, COMP, FMOD, GPT2, KHDRBS3, NCAPD3, REPS2, SFRP4, SLC15A2, SLC22A3 and VCAN; or
18 prostate cancer markers: ACADL, ANPEP, ANTXR1, AZGP1, CHRNA2, COL1A1, COL3A1, COMP, FMOD, GPT2, ITGBL1, KHDRBS3, NCAPD3, REPS2, SFRP4, SLC15A2, SLC22A3 and SPARC; or
39 prostate cancer markers: ACADL, AFF3, ANO7, ANPEP, ANTXR1, ASPN, AZGP1, CD38, CDH11, CHRNA2, COL10A1, COL1A1, COL1A2, COL3A1, COL8A1, COMP, CPXM2, CXCL14, FAM3B, FMOD, FRZB, GPT2, HGD, ITGBL1, KHDRBS3, MGP, MS4A6A, NCAPD3, NOX4, REPS2, SFRP2, SFRP4, SLC15A2, SLC22A3, SPARC, STXBP6, SULF1, THBS2 and VCAN,
d) comparing said molecular signature to a reference signature, and
e) assigning the subject to a low-risk of prostate cancer recurrence group based on the correlation of the molecular signature with the reference signature, thereby predicting the risk of cancer recurrence in said subject; and
(2) placing said subject under active surveillance.

2. The method according to claim 1, wherein said sample is a prostate biopsy sample, a prostate fine-needle aspirate sample, a prostate resection sample or a prostate tissue sample after prostatectomy.

3. The method according to claim 1, wherein said sample is a bodily fluid.

4. The method according to claim 3, wherein said bodily fluid is selected from the group consisting of blood, plasma, serum, lymph, ascetic fluid, cystic fluid, urine, bile, nipple exudate, synovial fluid, bronchoalveolar lavage fluid, sputum, amniotic fluid, peritoneal fluid, cerebrospinal fluid, pleural fluid, pericardial fluid, semen, saliva, sweat and alveolar macrophages.

5. The method according to claim 1, wherein the subject underwent prostatectomy and/or treatment by irradiation.

6. The method according to claim 1, wherein the reference signature is derived from the measurement of the expression levels of prostate cancer markers in a reference population comprising at least 100, at least 250, or at least 500 subjects diagnosed with prostate cancer of known prostate cancer recurrence status.

7. The method according to claim 1, wherein the subject is assigned to a low-risk of prostate cancer recurrence group, if the expression profile of ANPEP, AZGP1 and CHRNA2 is overexpressed with respect to a reference signature of a population of subjects diagnosed with aggressive prostate cancer, and the expression profile of COMP, KHDRBS3 and SFRP4 is underexpressed with respect to a reference signature of a population of subjects diagnosed with aggressive prostate cancer.

8. The method according to claim 1, wherein the subject is assigned to a low-risk of prostate cancer recurrence group, if the expression profile of ANPEP, AZGP1 and CHRNA2 is overexpressed with respect to a reference signature of a population of subjects diagnosed with aggressive prostate cancer, and the expression profile of ANTXR1, COMP, KHDRBS3, MS4A6A and SFRP4 is underexpressed with respect to a reference signature of a population of subjects diagnosed with aggressive prostate cancer.

9. The method according to claim 1, wherein the subject is assigned to a low-risk of prostate cancer recurrence group, if the expression profile of ACADL, ANPEP, AZGP1, CHRNA2, FMOD, GPT2, NCAPD3, REPS2, SLC15A2 and SLC22A3 is overexpressed with respect to a reference signature of a population of subjects diagnosed with aggressive prostate cancer, and the expression profile of COL1A1, COMP, KHDRBS3, SFRP4 and VCAN is underexpressed with respect to a reference signature of a population of subjects diagnosed with aggressive prostate cancer.

10. The method according to claim 1, wherein the subject is assigned to a low-risk of prostate cancer recurrence group, if the expression profile of ACADL, ANPEP, AZGP1, CHRNA2, FMOD, GPT2, NCAPD3, REPS2, SLC15A2 and SLC22A3 is overexpressed with respect to a reference signature of a population of subjects diagnosed with aggressive prostate cancer, and the expression profile of ANTXR1, COL1A1, COL3A1, COMP, ITGBL1, KHDRBS3, SFRP4 and SPARC is underexpressed with respect to a reference signature of a population of subjects diagnosed with aggressive prostate cancer.

11. The method according to claim 1, wherein the subject is assigned to a low-risk of prostate cancer recurrence group, if the expression profile of ACADL, AFF3, ANO7, ANPEP, AZGP1, CD38, CHRNA2, FAM3B, FMOD, GPT2, HGD, NCAPD3, REPS2, SLC15A2, SLC22A3 and STXBP6 is overexpressed with respect to a reference signature of a population of subjects diagnosed with aggressive prostate cancer, and the expression profile of ANTXR1, ASPN, CDH11, COL1A1, COL1A2, COL3A1, COL8A1, COL10A1, COMP, CPXM2, CXCL14, FRZB, ITGBL1, KHDRBS3, MGP, MS4A6A, NOX4, SFRP2, SFRP4, SPARC, SULF1, THBS2 and VCAN is underexpressed with respect to a reference signature of a population of subjects diagnosed with aggressive prostate cancer.

12. The method according to claim 1, wherein the subject is assigned to a low recurrence risk group if the molecular signature of the sample from said subject has the highest correlation with respect to a reference signature of a population of subjects previously diagnosed with indolent prostate cancer.

* * * * *

SEQUENCE LISTING

```
<160> NUMBER OF SEQ ID NOS: 39

<210> SEQ ID NO 1
<211> LENGTH: 50
<212> TYPE: DNA
<213> ORGANISM: Artificial Sequence
<220> FEATURE:
<223> OTHER INFORMATION: ILMN_1677636 (COMP)

<400> SEQUENCE: 1
agaggactat gagacccatc agctgcggca agcctaggga ccagggtgag          50

<210> SEQ ID NO 2
<211> LENGTH: 50
<212> TYPE: DNA
<213> ORGANISM: Artificial Sequence
<220> FEATURE:
<223> OTHER INFORMATION: ILMN_1672776 (COL10A1)

<400> SEQUENCE: 2
cccctaaaat atttctgatg gtgcactact ctgaggcctg tatggcccct          50

<210> SEQ ID NO 3
<211> LENGTH: 50
<212> TYPE: DNA
<213> ORGANISM: Artificial Sequence
<220> FEATURE:
<223> OTHER INFORMATION: ILMN_1684158 (GPT2)

<400> SEQUENCE: 3
cctgtggctg ttttcccgtc taggttctca caggtatctc ctgacagagg          50

<210> SEQ ID NO 4
<211> LENGTH: 50
<212> TYPE: DNA
<213> ORGANISM: Artificial Sequence
<220> FEATURE:
<223> OTHER INFORMATION: ILMN_1653719 (ITGBL1)

<400> SEQUENCE: 4
ggggacaatg aagacaagca cacaggaggt agaatatcag agtggggctg          50

<210> SEQ ID NO 5
<211> LENGTH: 50
<212> TYPE: DNA
<213> ORGANISM: Artificial Sequence
<220> FEATURE:
<223> OTHER INFORMATION: ILMN_1735996 (NOX4)

<400> SEQUENCE: 5
```

-continued tgaggagctg aacttgctca atctaaggct gattgtcgtg ttcctctttta    50

<210> SEQ ID NO 6
<211> LENGTH: 50
<212> TYPE: DNA
<213> ORGANISM: Artificial Sequence
<220> FEATURE:
<223> OTHER INFORMATION: ILMN_1810172 (SFRP4)

<400> SEQUENCE: 6
gttcaggaca agaagaaaac agccgggcgc accagtcgta gtaatccccc    50

<210> SEQ ID NO 7
<211> LENGTH: 50
<212> TYPE: DNA
<213> ORGANISM: Artificial Sequence
<220> FEATURE:
<223> OTHER INFORMATION: ILMN_1691747 (KHDRBS3)

<400> SEQUENCE: 7
aggcaccttc agcgaggaca gcaaagggcg tctacagaga ccagccatat    50

<210> SEQ ID NO 8
<211> LENGTH: 50
<212> TYPE: DNA
<213> ORGANISM: Artificial Sequence
<220> FEATURE:
<223> OTHER INFORMATION: ILMN_1683441 (NCAPD3)

<400> SEQUENCE: 8
tgtggaacac gagagctcct cctcaggggc ctggcactca ccttctattc    50

<210> SEQ ID NO 9
<211> LENGTH: 50
<212> TYPE: DNA
<213> ORGANISM: Artificial Sequence
<220> FEATURE:
<223> OTHER INFORMATION: ILMN_1875691 (ASPN)

<400> SEQUENCE: 9
cgtgtatgtg actcagtttc catggcttaa ctgtttctgc tggcataacc    50

<210> SEQ ID NO 10
<211> LENGTH: 50
<212> TYPE: DNA
<213> ORGANISM: Artificial Sequence
<220> FEATURE:
<223> OTHER INFORMATION: ILMN_1656934 (REPS2)

<400> SEQUENCE: 10 cccccatgg ttcaagtgac agtgggtgac cttgtctgcc aagatctttc    50

<210> SEQ ID NO 11
<211> LENGTH: 50
<212> TYPE: DNA
<213> ORGANISM: Artificial Sequence
<220> FEATURE:
<223> OTHER INFORMATION: ILMN_1687301 (VCAN)

<400> SEQUENCE: 11
cagccatagg tgcagtttgc ttctacatga tgctaaaggc tgcgaatggg    50

<210> SEQ ID NO 12
<211> LENGTH: 50
<212> TYPE: DNA
<213> ORGANISM: Artificial Sequence

<220> FEATURE:
<223> OTHER INFORMATION: ILMN_1701308 (COL1A1)

<400> SEQUENCE: 12
tccctcctag tctgtcctgc gtcctctgtc cccgggtttc agagacaact            50

<210> SEQ ID NO 13
<211> LENGTH: 50
<212> TYPE: DNA
<213> ORGANISM: Artificial Sequence
<220> FEATURE:
<223> OTHER INFORMATION: ILMN_1670379 (ANTXR1)

<400> SEQUENCE: 13
accatgctat aggagactgg gcaaaacctg tacaatgaca accctggaag            50

<210> SEQ ID NO 14
<211> LENGTH: 50
<212> TYPE: DNA
<213> ORGANISM: Artificial Sequence
<220> FEATURE:
<223> OTHER INFORMATION: ILMN_1678842 (THBS2)

<400> SEQUENCE: 14
gactgtcaac agcgtgcagg ttttctgttt ctgtgttgtg gggtcaaccg            50

<210> SEQ ID NO 15
<211> LENGTH: 50
<212> TYPE: DNA
<213> ORGANISM: Artificial Sequence
<220> FEATURE:
<223> OTHER INFORMATION: ILMN_1672611 (CDH11)

<400> SEQUENCE: 15
cgtgccagat ataactgtct tgtttcagtg agagacgccc tatttctatg            50

<210> SEQ ID NO 16
<211> LENGTH: 50
<212> TYPE: DNA
<213> ORGANISM: Artificial Sequence
<220> FEATURE:
<223> OTHER INFORMATION: ILMN_2198239 (HGD)

<400> SEQUENCE: 16
gggagccact caagagccac ttcactccca actccaggaa cccagcagaa            50

<210> SEQ ID NO 17
<211> LENGTH: 50
<212> TYPE: DNA
<213> ORGANISM: Artificial Sequence
<220> FEATURE:
<223> OTHER INFORMATION: ILMN_1698849 (CHRNA2)

<400> SEQUENCE: 17
tcattcctct ccttccttgc tgcaaaatgg ctctgcacca gccggccccc            50

<210> SEQ ID NO 18
<211> LENGTH: 50
<212> TYPE: DNA
<213> ORGANISM: Artificial Sequence
<220> FEATURE:
<223> OTHER INFORMATION: ILMN_1796734 (SPARC)

<400> SEQUENCE: 18
cgcagctccc caatcacact agcaacattt caagtgcttg agagccatgc            50

<210> SEQ ID NO 19
<211> LENGTH: 50
<212> TYPE: DNA
<213> ORGANISM: Artificial Sequence
<220> FEATURE:
<223> OTHER INFORMATION: ILMN_1797154 (AZGP1)

<400> SEQUENCE: 19
tgaggagcag tgtgggggga cagacaggag gtggatttgg agaccgaaga          50

<210> SEQ ID NO 20
<211> LENGTH: 50
<212> TYPE: DNA
<213> ORGANISM: Artificial Sequence
<220> FEATURE:
<223> OTHER INFORMATION: ILMN_2211739 (SLC15A2)

<400> SEQUENCE: 20
cttgtgcagt gttgctggag ctggcctggt gtctccaaat gaccatgaaa          50

<210> SEQ ID NO 21
<211> LENGTH: 50
<212> TYPE: DNA
<213> ORGANISM: Artificial Sequence
<220> FEATURE:
<223> OTHER INFORMATION: ILMN_1748323 (CXCL14)

<400> SEQUENCE: 21
cctctgtaca tataccctta agaacgcccc ctccacacac tgcccccag          50

<210> SEQ ID NO 22
<211> LENGTH: 50
<212> TYPE: DNA
<213> ORGANISM: Artificial Sequence
<220> FEATURE:
<223> OTHER INFORMATION: ILMN_2172969 (STXBP6)

<400> SEQUENCE: 22
gattttgctc cttgcatagt aatcttttgc atgaaccatc accagcgttc          50

<210> SEQ ID NO 23
<211> LENGTH: 50
<212> TYPE: DNA
<213> ORGANISM: Artificial Sequence
<220> FEATURE:
<223> OTHER INFORMATION: ILMN_1683824 (ANO7)

<400> SEQUENCE: 23
gctcacaagg ccctctttgt ttcctgctcc cagacataag cccaaggggc          50

<210> SEQ ID NO 24
<211> LENGTH: 50
<212> TYPE: DNA
<213> ORGANISM: Artificial Sequence
<220> FEATURE:
<223> OTHER INFORMATION: ILMN_1741688 (CPXM2)

<400> SEQUENCE: 24
ccagaagtgg ggtggcctga agccctctct ctgcttgagg tattgcccct          50

<210> SEQ ID NO 25
<211> LENGTH: 50
<212> TYPE: DNA
<213> ORGANISM: Artificial Sequence
<220> FEATURE:
<223> OTHER INFORMATION: ILMN_2359800 (MS4A6A)

<400> SEQUENCE: 25
gggactatcc agatcttgtg tggcatgatg gtattgagct tggggatcat      50

<210> SEQ ID NO 26
<211> LENGTH: 50
<212> TYPE: DNA
<213> ORGANISM: Artificial Sequence
<220> FEATURE:
<223> OTHER INFORMATION: ILMN_1660890 (ACADL)

<400> SEQUENCE: 26
gaagctggaa gccatcatac cttactgcct tgaaacccct aggactcagc      50

<210> SEQ ID NO 27
<211> LENGTH: 50
<212> TYPE: DNA
<213> ORGANISM: Artificial Sequence
<220> FEATURE:
<223> OTHER INFORMATION: ILMN_1722898 (SFRP2)

<400> SEQUENCE: 27
ggcccaaact tgtgggtcac aaaccctgtt gagataaagc tggctgttat      50

<210> SEQ ID NO 28
<211> LENGTH: 50
<212> TYPE: DNA
<213> ORGANISM: Artificial Sequence
<220> FEATURE:
<223> OTHER INFORMATION: ILMN_1702363 (SULF1)

<400> SEQUENCE: 28
cctcactgag tcatcagtac cctcctattc agctccccaa gatgatgtgt      50

<210> SEQ ID NO 29
<211> LENGTH: 50
<212> TYPE: DNA
<213> ORGANISM: Artificial Sequence
<220> FEATURE:
<223> OTHER INFORMATION: ILMN_2048478 (SLC22A3)

<400> SEQUENCE: 29
ctgagatctg ggtttaacga tctgggcttt gtcatggtgt tttacgttcg      50

<210> SEQ ID NO 30
<211> LENGTH: 50
<212> TYPE: DNA
<213> ORGANISM: Artificial Sequence
<220> FEATURE:
<223> OTHER INFORMATION: ILMN_2233783 (CD38)

<400> SEQUENCE: 30
tacatgactc agcatacctg ctggtgcaga gctgaagatt ttggagggtc      50

<210> SEQ ID NO 31
<211> LENGTH: 50
<212> TYPE: DNA
<213> ORGANISM: Artificial Sequence
<220> FEATURE:
<223> OTHER INFORMATION: ILMN_1716246 (FRZB)

<400> SEQUENCE: 31
gcctgattga gaagcacaac tgaaaccagt agccgctggg gtgttaatgg      50

<210> SEQ ID NO 32

```
<211> LENGTH: 50
<212> TYPE: DNA
<213> ORGANISM: Artificial Sequence
<220> FEATURE:
<223> OTHER INFORMATION: ILMN_1685433 (COL8A1)

<400> SEQUENCE: 32
gagaccgggt gttcctccag atgccctcag aacaggctgc aggactgtat          50

<210> SEQ ID NO 33
<211> LENGTH: 50
<212> TYPE: DNA
<213> ORGANISM: Artificial Sequence
<220> FEATURE:
<223> OTHER INFORMATION: ILMN_1773079 (COL3A1)

<400> SEQUENCE: 33
tcaactgctt gtaaaggtgc tcctcttttt tcttgtcatt gctggtcaag          50

<210> SEQ ID NO 34
<211> LENGTH: 50
<212> TYPE: DNA
<213> ORGANISM: Artificial Sequence
<220> FEATURE:
<223> OTHER INFORMATION: ILMN_1651958 (MGP)

<400> SEQUENCE: 34
ggagcctctc tccctactgc tgctacacaa gaccctgaga ctgacctgca          50

<210> SEQ ID NO 35
<211> LENGTH: 50
<212> TYPE: DNA
<213> ORGANISM: Artificial Sequence
<220> FEATURE:
<223> OTHER INFORMATION: ILMN_2355486 (FAM3B)

<400> SEQUENCE: 35
ctggaccgat gacaaagttt attcagagtg ctgctccaaa atccctgctc          50

<210> SEQ ID NO 36
<211> LENGTH: 50
<212> TYPE: DNA
<213> ORGANISM: Artificial Sequence
<220> FEATURE:
<223> OTHER INFORMATION: ILMN_1789639 (FMOD)

<400> SEQUENCE: 36
ggggcaagga ctgttggagg agagttagcc caagtatagg ctctgcccag          50

<210> SEQ ID NO 37
<211> LENGTH: 50
<212> TYPE: DNA
<213> ORGANISM: Artificial Sequence
<220> FEATURE:
<223> OTHER INFORMATION: ILMN_2104356 (COL1A2)

<400> SEQUENCE: 37
gatccacatt gttaggtgct gacctagaca gagatgaact gaggtccttg          50

<210> SEQ ID NO 38
<211> LENGTH: 50
<212> TYPE: DNA
<213> ORGANISM: Artificial Sequence
<220> FEATURE:
<223> OTHER INFORMATION: ILMN_1775235 (AFF3)

<400> SEQUENCE: 38
```

```
gtagattccc aagagacttt agcagtcacc agccttaatg catgtacagg          50

<210> SEQ ID NO 39
<211> LENGTH: 50
<212> TYPE: DNA
<213> ORGANISM: Artificial Sequence
<220> FEATURE:
<223> OTHER INFORMATION: ILMN_1763837 (ANPEP)

<400> SEQUENCE: 39
ctccagccca cgttctctct gcctgtgagc cagtctagtt cctgatgacc          50
```